US012390810B2

(12) United States Patent
Heller et al.

(10) Patent No.: US 12,390,810 B2
(45) Date of Patent: Aug. 19, 2025

(54) ELECTROKINETIC MICROELECTRODE DEVICES AND METHODS FOR BIOMARKER ANALYSIS

(71) Applicant: THE REGENTS OF THE UNIVERSITY OF CALIFORNIA, Oakland, CA (US)

(72) Inventors: Michael J. Heller, Portland, OR (US); Daniel Heineck, Tigard, OR (US); Stuart D. Ibsen, Portland, OR (US); Sadik Esener, Portland, OR (US); Jean M. Lewis, San Diego, CA (US)

( * ) Notice: Subject to any disclaimer, the term of this patent is extended or adjusted under 35 U.S.C. 154(b) by 850 days.

(21) Appl. No.: 17/753,176

(22) PCT Filed: Aug. 21, 2020

(86) PCT No.: PCT/US2020/047519
§ 371 (c)(1),
(2) Date: Feb. 22, 2022

(87) PCT Pub. No.: WO2021/041259
PCT Pub. Date: Mar. 4, 2021

(65) Prior Publication Data
US 2022/0274111 A1  Sep. 1, 2022

Related U.S. Application Data

(60) Provisional application No. 62/891,204, filed on Aug. 23, 2019.

(51) Int. Cl.
*B01L 3/00* (2006.01)
*A61B 5/157* (2006.01)
(Continued)

(52) U.S. Cl.
CPC ........ *B01L 3/502761* (2013.01); *A61B 5/157* (2013.01); *B01L 3/502715* (2013.01);
(Continued)

(58) Field of Classification Search
CPC ..... B01L 2300/0636; B01L 2400/0415; G01N 27/44721; C12Q 1/686
See application file for complete search history.

(56) References Cited

U.S. PATENT DOCUMENTS 5,849,486 A   12/1998 Heller et al.
5,929,208 A   7/1999 Heller et al.
(Continued)

FOREIGN PATENT DOCUMENTS

WO    2008138006 A2    11/2008

OTHER PUBLICATIONS

Barrese, J.C. et al. "Scanning electron microscopy of chronically implanted intracortical microelectrode arrays in non-human primates", J. Neural Eng., vol. 13, No. 2, p. 026 003, Jan. 2016.
(Continued)

*Primary Examiner* — Young J Kim
(74) *Attorney, Agent, or Firm* — Perkins Coie LLP

(57) ABSTRACT

Disclosed are miniaturized electronic systems, devices and methods for biomarker analysis, which can be incorporated into blood collection tubes and other containers that enable the immediate isolation, concentration, analysis and storage of disease related biomarkers upon blood draw. In some aspects, a miniaturized electronic system includes a high-surface area folded or sandwiched electrokinetic microelectrode array chip device that allows both AC dielectrophoretic (DEP) and DC electrophoretic based separation and isolation and other processes to be used for the concentration and biomarkers.

7 Claims, 11 Drawing Sheets

(51) Int. Cl.

| | |
|---|---|
| B03C 5/00 | (2006.01) |
| B03C 5/02 | (2006.01) |
| C12Q 1/686 | (2018.01) |
| G01N 27/447 | (2006.01) |

(52) U.S. Cl.
CPC ............... *B03C 5/005* (2013.01); *B03C 5/02* (2013.01); *G01N 27/44721* (2013.01); *G01N 27/44791* (2013.01); *B01L 2200/0647* (2013.01); *B01L 2300/0636* (2013.01); *B01L 2300/0645* (2013.01); *B01L 2400/0415* (2013.01)

(56) References Cited

U.S. PATENT DOCUMENTS

| | | |
|---|---|---|
| 6,017,696 A | 1/2000 | Heller |
| 6,048,690 A | 4/2000 | Heller et al. |
| 6,051,380 A | 4/2000 | Sosnowski et al. |
| 6,129,828 A | 10/2000 | Sheldon et al. |
| 6,238,624 B1 | 5/2001 | Heller et al. |
| 6,245,508 B1 | 6/2001 | Heller et al. |
| 6,306,348 B1 | 10/2001 | Havens et al. |
| 6,379,897 B1 | 4/2002 | Weidenhammer et al. |
| 6,403,367 B1 | 6/2002 | Cheng et al. |
| 6,488,832 B2 | 12/2002 | Heller |
| 6,492,122 B2 | 12/2002 | Weidenhammer et al. |
| 6,518,022 B1 | 2/2003 | Sosnowski et al. |
| 6,569,382 B1 | 5/2003 | Edman et al. |
| 6,582,660 B1 | 6/2003 | Heller et al. |
| 6,652,808 B1 | 11/2003 | Heller et al. |
| 6,682,936 B2 | 1/2004 | Kovacs |
| 6,706,473 B1 | 3/2004 | Edman et al. |
| 6,780,584 B1 | 8/2004 | Edman et al. |
| 6,824,740 B1 | 11/2004 | Sheldon et al. |
| 7,060,224 B2 | 6/2006 | Edman et al. |
| 7,101,661 B1 | 9/2006 | Heller et al. |
| 7,172,864 B1 | 2/2007 | Heller et al. |
| 7,172,896 B2 | 2/2007 | Cheng et al. |
| 7,300,757 B2 | 11/2007 | Edman et al. |
| 7,314,708 B1 | 1/2008 | Heller et al. |
| 7,704,726 B2 | 4/2010 | Heller et al. |
| 7,857,957 B2 | 12/2010 | Cheng et al. |
| 7,947,486 B2 | 5/2011 | Heller et al. |
| 8,114,589 B2 | 2/2012 | Sosnowski et al. |
| 8,202,689 B2 | 6/2012 | Heller et al. |
| 8,313,940 B2 | 11/2012 | Heller et al. |
| 8,389,212 B1 | 3/2013 | Heller et al. |
| 8,603,791 B2 | 12/2013 | Krishnan et al. |
| 8,815,554 B2 | 8/2014 | Krishnan et al. |
| 8,815,555 B2 | 8/2014 | Krishnan et al. |
| 8,871,481 B2 | 10/2014 | Krishnan et al. |
| 8,877,470 B2 | 11/2014 | Krishnan et al. |
| 8,932,447 B2 | 1/2015 | Heller et al. |
| 8,932,815 B2 | 1/2015 | Krishnan et al. |
| 8,969,059 B2 | 3/2015 | Krishnan et al. |
| 9,005,941 B2 | 4/2015 | Krishnan et al. |
| 9,034,578 B2 | 5/2015 | Krishnan et al. |
| 9,034,579 B2 | 5/2015 | Krishnan et al. |
| 9,206,416 B2 | 12/2015 | Krishnan et al. |
| 9,387,489 B2 | 7/2016 | Charlot et al. |
| 9,499,812 B2 | 11/2016 | Krishnan et al. |
| 9,682,385 B2 | 6/2017 | Charlot et al. |
| 9,827,565 B2 | 11/2017 | Krishnan et al. |
| 10,006,083 B2 | 6/2018 | Krishnan et al. |
| 10,232,369 B2 | 3/2019 | Turner et al. |
| 2008/0047832 A1 | 2/2008 | Cheng et al. |
| 2019/0090791 A1 | 3/2019 | Siu et al. |

OTHER PUBLICATIONS

Barrett, A.N. et al. "Implementing prenatal diagnosis based on cell-free fetal DNA: Accurate identification of factors affecting fetal DNA yield", PLoS One, vol. 6, No. 10, e25202, 2011.

Benke, G. et al. "The electrochemical dissolution of platinum", Hydrometallurgy, vol. 64, No. 3, pp. 205-218, Jun. 2002.

Bentley, R. et al. "The alternating current electrolysis of concentrated acids", Journal of Applied Chemistry, vol. 7, No. 11, pp. 619-626, May 1957.

Ben-Yaakov, D. et al. "Dielectric decrement as a source of ion-specic e ects", The Journal of Chemical Physics, vol. 134, No. 7, p. 074 705, 2011.

Bisceglia, E. et al. "A generic and label free method based on dielectrophoresis for the continuous separation of microorganism from whole blood samples", Sensors and Actuators B: Chemical, vol. 212, pp. 335-343, Jun. 2015.

Black, R.C. et al. "Dissolution of smooth platinum electrodes in biological fluids.", eng, Appl Neurophysiol, vol. 42, No. 6, pp. 366-374, 1980.

Briner, E. et al. "Recherches sur l'electrolyse avec courant ondule. III. observations sur l'attaque des electrodes de platine et la formation de l'ozone sous l'e et du courant alternatif et du courant ondule, a differentes frequences et a differentes concentrations des so", Helvetica Chimica Acta, vol. 26, No. 6, pp. 1829-1835, Oct. 1943.

Brown, M.A. et al. "Effect of electrolyte concentration on the stern layer thickness at a charged interface", Angewandte Chemie International Edition, vol. 55, No. 11, pp. 3790-3794, Feb. 2016.

Brown, S.A. et al. "Electrochemical corrosion in saline and serum" Journal of Biomedical Materials Research, vol. 14, No. 2, pp. 173-175, Mar. 1980.

Castellanos, A. et al. "Electro-hydrodynamics and dielectrophoresis in microsystems: Scaling laws", Journal of Physics D: Applied Physics, vol. 36, No. 20, p. 2584, 2003.

Castro, E.R. et al. "Present state of microchip electrophoresis: State of the art and routine applications", Journal of Chromatography A, vol. 1382, pp. 66-85, Feb. 2015.

Chen, D.F. et al. "Simulation studies on electrothermal fluid flow induced in a dielectrophoretic microelectrode system", Journal of Micromechanics and Microengineering, vol. 16, No. 11, p. 2411, 2006.

Cheng J, et al. "Preparation and Hybridization Analysis of DNA/RNA from *E. coli* on Microfabricated Bioelectronic Chips", Nature Biotechnology, vol. 16, pp. 541-546, 1998.

Cheng, J. et al. "Isolation of Cultured Cervical Carcinoma Cells Mixed with Peripheral Blood Cells on a Bioelectronic Chip", Analytical Chemistry, vol. 70, #11, pp. 2321-2326, 1998.

Chin, C.D. et al. "Commercialization of micro fluidic point-of-care diagnostic devices", Lab on a Chip, vol. 12, No. 12, p. 2118, 2012.

Chuang, C.H. et al. "Lab on a chip for multiplexed immunoassays to detect bladder cancer using multifunctional dielectrophoretic manipulations", Lab Chip, vol. 15, No. 14, pp. 3056-3064, 2015.

Craggs, M.D. et al. "Performance of platinum stimulating electrodes, mapped on the limitvoltage plane", Medical & Biological Engineering & Computing, vol. 24, No. 4, pp. 424-430, Jul. 1986.

Czarnetzki, L.R. et al. "Formation of hypochlorite, chlorate and oxygen during NaCl electrolysis from alkaline solutions at an $RuO_2/TiO_2$ anode", J Appl Electrochem, vol. 22, No. 4, pp. 315-324, Apr. 1992.

Daniel M. et al. "Selective DNA attachment of particles to substrates" Journal of Materials Research, vol. 17, No. 2, Feb. 2002, pp. 473-478.

Dehlinger D. et al. "Next Generation Microelectronic Array Devices", in Handbook of Nanotechnology, Bhushan, B (Ed). Part B, Chapter 14, Springer, pp. 401-413, 2006.

Dehlinger D. et al. "Reconfigurable CMOS Electronic Microarray System for the Assisted Self-Assembly of Higher-Order Nanostructures", in Nanomanufacturing Handbook, Busnaina A (Ed), Chapter 5, CRC Press, pp. 107-126, 2006.

Dehlinger DA et al. "Electric Field Assisted Assembly of Functionalized Quantum Dots into Multi Layer Thin Films", NISTI-Nanotech 2006, vol. 1, Chap. 4, pp. 389-392, 2006.

Delgado, V.A. et al. "Measurement and interpretation of electrokinetic phenomena (IUPAC technical report)", Pure and Applied Chemistry, vol. 77, No. 10, Jan. 2005.

Edman, C. et al. "Electric Field Directed Nucleic Acid Hybridization on Microchips" Nucleic Acids Research, vol. 25, #24, pp. 4907-4914, 1997.

(56) References Cited

OTHER PUBLICATIONS

Edman, C.F. et al. "Electric Field Directed Assembly of an InGaAs LED onto Silicon Circuitry", IEEE—Photonics Technology Letters, v12, #9, 1198-2000, 2000.
Ellison, W. et al. "New permittivity measurements of seawater", Radio Science, vol. 33, No. 3, pp. 639-648, May 1998.
Esener, S. et al. "DNA Assisted Micro-Assembly: A Heterogeneous Integration Technology For Optoelectronics," Proc. SPIE Critical Reviews of Optical Science and Technology, Heterogeneous Integration, Ed. A. Hussain, CR70, Chapter 7, Jan. 1998.
Fang, X. et al. "Electrophysiological and histological studies of chronically implanted intrapapillary microelectrodes in rabbit eyes", Graefe's Arch Clin Exp Ophthalmo, vol. 244, No. 3, pp. 364-375, Aug. 2005.
Fernandez, R.E. et al. "Aptamer-functionalized graphene-gold nanocomposites for label-free detection of dielectrophoretic-enriched neuropeptide y", Electrochemistry Communications, vol. 72, pp. 144-147, Nov. 2016.
Franks, W. et al. "Impedance characterization and modeling of electrodes for biomedical applications", IEEE Transactions on Biomedical Engineering, vol. 52, No. 7, pp. 1295-1302, Jul. 2005.
Gahan, P.B. "Circulating nucleic acids in early diagnosis, prognosis and treatment monitoring" Advances in Predictive, Preventive and Personalised Medicine. Springer, 2015, vol. 5.
Gonzalez, A. et al. "Electrothermal flows generated by alternating and rotating electric elds in microsystems", J. Fluid Mech., vol. 564, p. 415, Sep. 2006.
Gu, W.Y. et al. "Diffusivity of ions in agarose gels and intervertebral disc: Effect of porosity", Annals of Biomedical Engineering, vol. 32, No. 12, pp. 1710-1717, Dec. 2004.
Gurtner C, et al. "Microelectronic Array Devices and Techniques for Electric Field Enhanced DNA Hybridization In Low-Conductance Buffers" Electrophoresis 2002, 23, 1543-1550.
Gurtner, C. et al. "Photoelectrophoretic Transport and Hybridization of DNA Oligonucleotides on Unpatterned Silicon Substrates", J. Am. Chem. Soc., v122, #36, pp. 8589-8594, 2000.
Hartmann et al. "Stable 16-year storage of DNA purified with the QIAamp ® DNA Blood Mini Kit" Oct. 2016. 4 pages.
Haus, H.A. et al. "Electromagnetic fields and energy" Prentice-Hall: Englewood Clis, NJ, 1989.
Hayes, M. et al. "Aggregation effects on the electrocatalytic activity of platinum", Journal of Catalysis, vol. 53, No. 1, pp. 88-95, 1978, issn: 0021-9517.
Heineck D.P. et al. "Electrokinetic device design and constraints for use in high conductance solutions", Electrophoresis, 2017.
Heller M, et al. "Electric Field Devices for Assisted Assembly of DNA Nanocomponents and Other Nanofabrication Applications", in BioMEMS and Biomedical Nanotechnology VI, Heller MJ, Ozkan M, and Ferrari M (Eds), Springer, vol. 2, Chapter 6, pp. 139-159, 2006.
Heller M. "DNA Microarray Technology: Devices, Systems and Applications", In Annual Review of Biomedical Engineering, 2002, 4:129-53.
Heller M. "Integrated Microfabricated Biodevices: Advanced Technologies for Genomics Drug Discovery, Bioanalysis, and Clinical Diagnostics" 2001. 462 pages.
Heller M. et al. "Detection of Cancer Related DNA Nanoparticulate Biomarkers and Nanoparticles in Whole Blood" TechConnect World 2010 Proceedings, Nanotechnology 2010, vol. 3, Chap. 6, Cancer Nanotechnology pp. 372-375.
Heller M. et al. "Parallel Assisted Assembly of Multilayer DNA and Protein Nanoparticle Structures Using a CMOS Electronic Array" DNA-Based Nanoscale Integration Symposium, W. Fritzsche (Ed), American Institute of Physics, NY, pp. 73-81, 2006.
Heller, M. "An Active Microelectronic Device For Multiplex DNA Analysis", IEEE Engineering In Medicine And Biology, pp. 100-104, Mar./Apr. 1996.
Heller, M. et al. "Active Microelectronic Arrays for DNA Hybridization Analysis" in DNA Microarrays: A Practical Approach, Edited by M. Schena, Oxford University Press, pp. 167-185, 1999.
Heller, M. et al. Active Microelectronic Chip Devices Which Utilize Controlled Electrophoretic Fields for Multiplex DNA Hybridization and Other Genomic Applications, Electrophoresis 2000, vol. 21, pp. 157-164, Jan. 2000.
Heller, M. et al. "An Integrated Microelectronic Hybridization System for Genomic Research and Diagnostic Applications", in Micro Total Analysis Systems 98, Edited by D. J. Harrison and A. van den Berg, Kluwer Academic Publishers, pp. 221-224, 1998.
Heller, M. et al. "Self-Assembling DNA Photonic Nanostructures", in Artificial Self-Assembling Systems for Gene Delivery, American Chemical Society, pp. 72-83, 1996.
Heller, M.J. et al. "Electric Field Process for the Fabrication of Higher Order Structures from Biomolecule Derivatized Nanoparticles" NISTI-Nanotech 2007, vol. 1, Chap.4, 269-271, 2007.
Hirschorn, B. et al. "Determination of effective capacitance and film thickness from constant-phase-element parameters", Electrochimica Acta, vol. 55, No. 21, pp. 6218-6227, Aug. 2010.
Hodko D. et al. "CMOS Microarrays for Diagnostic and Nanotechnology Applications", in CMOS Biotechnology, Lee H, Ham D and Westervelt (Ed.), Chapter 7, pp. 179-206, 2007.
Hoerter, J.A. et al. "Sirna-like double-stranded rnas are specifically protected against degradation in human cell extract", PloS one, vol. 6, No. 5, e20359, 2011.
Horbett, T.A. et al. "Cell adhesion to a series of hydrophili-hydrophobic copolymers studies with a spinning disc apparatus", Journal of Biomedical Materials Research, vol. 22, No. 5, pp. 383-404, May 1988.
Huang Y. et al. "Electric Manipulation of Bioparticles and Macromolecules on Microfabricated Electrodes", Analytical Chemistry 2001, (73):1549-59.
Huang, Y. et al. "Dielectrophoretic Cell Separation and Gene Expression Profiling on Microelectronic Chip Arrays", Anal. Chem. 2002, 74, 3362-71.
Hudak, E.M. et al. "Platinum for neural stimulation: Voltammetry considerations", J. Neural Eng., vol. 7, No. 2, p. 026 005, Mar. 2010. doi: 10.1088/1741-2560/7/2/026005.
Ibsen S. et al. "Rapid Isolation and Detection of Exosomes and Associated Biomarkers from Plasma", ACS Nano 2017, DOI: 10.1021/acsnano.7b00549.
Ibsen, S. et al. "Recovery of drug delivery nanoparticles from human plasma using an electrokinetic platform technology", Small, vol. 11, No. 38, pp. 5088-5096, Aug. 2015. doi: 10.1002/smll. 201500892.
Inci, F. et al. "Nanoplasmonic quantitative detection of intact viruses from unprocessed whole blood" ACS Nano, vol. 7, No. 6, pp. 4733-4745, Jun. 2013. doi: 10.1021/nn3036232.
Irimajiri, A. et al. "A dielectric theory of multi-stratified shell model with its application to a lymphoma cell", Journal of Theoretical Biology, vol. 78, No. 2, pp. 251-269, May 1979.
ISA, International Search Report and Written Opinion for PCT Application No. PCT/US2020/047519. Mail Date: Nov. 24, 2020. 10 pages.
Jones, T. "Basic theory of dielectrophoresis and electrorotation", IEEE Eng. Med. Biol. Mag., vol. 22, No. 6, pp. 33-42, Nov. 2003. doi: 10.1109/memb.2003.1304999.
Juchniewicz, R. "The influence of alternating current on the anodic behaviour of platinum", Platinum Metals Review, vol. 6, No. 3, pp. 100-105, 1962. [Online]. Available: http://www.ingentaconnect.com/content/matthey/pmr/1962/00000006/00000003/art00009.
Juchniewicz, R. "The influence of increasing superimposed 50 c/s a.c. on the anodic dissolution of platinum in 3% sodium chloride", Corrosion Science, vol. 6, No. 2, pp. 69-77, Jan. 1966. doi: 10.1016/s0010-938x(66)80026-4.
Kaatze, U. "Complex permittivity of water as a function of frequency and temperature", Journal of Chemical & Engineering Data, vol. 34, No. 4, pp. 371-374, Oct. 1989.
Kassengne SK, et al. Numerical Modeling of Transport and Accumulation of DNA on Electronically Active Biochips, Sensors and Actuators 2003, B 94, 81-98.
Kong, F.Y. et al. "A paper disk equipped with graphene/polyaniline/au nanoparticles/glucose oxidase biocomposite modified screen-printed electrode: Toward whole blood glucose determination", Biosensors and Bioelectronics, vol. 56, pp. 77-82, Jun. 2014.

(56) References Cited

OTHER PUBLICATIONS

Krishnan R. et al. "Alternating current electrokinetic separation and detection of DNA nanoparticles in high-conductance solutions" Electrophoresis, v. 29, #9, pp. 1765-1774, May 2008.

Krishnan R. et al. "An AC electrokinetic method for the enhanced detection of DNA nanoparticles", J. Biophotonics, V2, #4, pp. 253-261, 2009.

Krishnan R. et al. Rapid Isolation and Detection of Cell Free Circulating DNA and Other Disease Biomarkers Directly from Whole Blood, in Circulating Nucleic Acids in Plasma and Serum, 2011, Chap. 34, pp. 247-257.

Krishnan, R. et al. "Interaction of nanoparticles at the {dep} microelectrode interface under high conductance conditions", Electrochemistry Communications, vol. 11, No. 8, pp. 1661-1666, 2009.

Kuhn, A. et al. "The behaviour of platinum, iridium and ruthenium electrodes in strong chloride solutions", Journal of Electroanalytical Chemistry and Interfacial Electrochemistry, vol. 41, No. 3, pp. 329-349, Feb. 1973.

Lee, M.G. et al. "Label-free cancer cell separation from human whole blood using inertial micro fluidics at low shear stress", Analytical Chemistry, vol. 85, No. 13, pp. 6213-6218, Jul. 2013.

Lewis J.M. et al. "Integrated Analysis of Exosomal Protein Biomarkers on AC Electrokinetic Chips Enables Rapid Detection of Pancreatic Cancer in Patient Blood", ACS Nano (2018).

Lewis, J.M. et al. "Detecting cancer biomarkers in blood: Challenges for new molecular diagnostic and point-of-care tests using cell-free nucleic acids", Expert review of molecular diagnostics, vol. 15, No. 9, pp. 1187-1200, 2015.

Llopis, J. "Corrosion of platinum metals and chemisorption", Catalysis Re-views, vol. 2, No. 1, pp. 161-220, Jan. 1969.

Llopis, J. et al. "Electrochemical corrosion of platinum in hydrochloric acid solutions", Journal of The Electrochemical Society, vol. 108, No. 8, p. 720, 1961.

Llopis, J. et al. "Study of the impedance of a platinum electrode in the system cl2/cl-(HClO4aq)", Electrochimica Acta, vol. 8, No. 3, pp. 163-173, Mar. 1963.

Malmberg, C. et al. "Dielectric constant of water from 0 to 100 C", J Res Nat Bureau Stand, vol. 56, pp. 1-8, 1956.

Manouchehri, S. et al. "Dielectrophoretic recovery of DNA from plasma for the identification of chronic lymphocytic leukemia point mutations", Int. J. Hematol. Oncol., vol. 5, No. 1, pp. 27-35, May 2016.

Mathew, B. et al. "Dielectrophoresis based cell switching in continuous flow micro fluidic devices", Journal of Electrostatics, vol. 84, pp. 63-72, Dec. 2016.

McCanna, J.P. et al. "Low level epifluorescent detection of nanoparticles and DNA on dielectrophoretic microarrays" J. BioPhotonics, 1-11 (2013).

Oddoze, C. et al. "Stability study of 81 analytes in human whole blood, in serum and in plasma", Clinical Biochemistry, vol. 45, No. 6, pp. 464-469, Apr. 2012.

Park, K. et al. "Dielectrophoretic lab-on-CMOS platform for trapping and manipulation of cells", Biomedical Microdevices, vol. 18, No. 1, Jan. 2016.

Patrick, E. et al. "Corrosion of tungsten microelectrodes used in neural recording applications", Journal of Neuroscience Methods, vol. 198, No. 2, pp. 158-171, Jun. 2011.

Pethig, R. "Dielectrophoresis: Status of the theory, technology, and applications", Biomicrofluidics, vol. 4, No. 2, p. 022 811, 2010.

Pourbaix, M. et al. "Electrochemical properties of the platinum metals", Platinum metals review, vol. 3, No. 2, pp. 47-53, 1959.

Prasad, A. et al. "Comprehensive characterization and failure modes of tungsten microwire arrays in chronic neural implants", J. Neural Eng., vol. 9, No. 5, p. 056 015, Sep. 2012.

Pyell, U. "Characterization of nanoparticles by capillary electromigration separation techniques", Electrophoresis, vol. 31, No. 5, pp. 814-831, Mar. 2010.

Ramo, S. et al. Fields and waves in communication electronics. John Wiley & Sons Inc, Feb. 11, 1994, 864 Seiten.

Ramos, A. "Electrokinetics and electrohydrodynamics in microsystems" Springer Science Business Media, 2011.

Ramos, A. et al. "AC electric-field-induced fluid flow in microelectrodes", Journal of colloid and interface science, vol. 217, No. 2, pp. 420-422, 1999.

Rand, D. et al. "A study of the dissolution of platinum, palladium, rhodium and gold electrodes in 1 m sulphuric acid by cyclic voltammetry", Journal of Electroanalytical Chemistry and Interfacial Electrochemistry, vol. 35, No. 1, pp. 209-218, Mar. 1972.

Sanghavi, B.J. et al. "Ultrafast immunoassays by coupling dielectrophoretic biomarker enrichment in nanoslit channel with electrochemical detection on graphene", Lab Chip, vol. 15, No. 24, pp. 4563-4570, 2015.

Saucedo-Espinosa, M.A. et al. "Polarization behavior of polystyrene particles under direct current and low-frequency (1 kHz) electric elds in dielectrophoretic systems", Electrophoresis, vol. 37, No. 4, pp. 635-644, Dec. 2015.

Saville, D.A. "Electrohydrodynamics:the Taylor-melcher leaky dielectric model", Annu. Rev. Fluid Mech., vol. 29, No. 1, pp. 27-64, Jan. 1997.

Scott, M. et al. "Theoretical model of electrode polarization and AC electroosmotic fluid flow in planar electrode arrays", Journal of Colloid and Interface Science, vol. 238, No. 2, pp. 449-451, Jun. 2001.

Sharma, A. et al. "Rapid electrical immunoassay of the cardiac biomarker troponin i through dielectrophoretic concentration using imbedded electrodes", Biosensors and Bioelectronics, vol. 82, pp. 78-84, Aug. 2016.

Shepherd, B. et al. "Scanning electron microscopy of platinum scala tympani electrodes following chronic stimulation in patients", Biomaterials, vol. 12, No. 4, pp. 417-423, May 1991.

Song, H. et al. "Continuous-flow sorting of stem cells and differentiation products based on dielectrophoresis", Lab on a Chip, vol. 15, No. 5, pp. 1320-1328, 2015.

Song, Y. et al. "Device for dielectrophoretic separation and collection of nanoparticles and DNA under high conductance conditions", Electrophoresis, vol. 36, No. 9-10, pp. 1107-1114, Apr. 2015.

Sonnenberg A. et al. "Dielectrophoretic Isolation and Detection of Cancer Related Circulating Cell Free DNA Biomarkers from Blood and Plasma", Electrophoresis, V35, 12-13, pp. 1828-1836, Jul. 2014.

Sonnenberg A. et al. "Rapid Electrokinetic Isolation of Cancer-Related Circulating Cell Free DNA Directly from Blood", Clinical Chemistry, 60:3, pp. 500-509, 2014.

Sonnenberg, A. et al. "Dielectrophoretic Isolation and Detection of cfc-DNA Nanoparticulate Biomarkers and Virus form Blood", Electrophoresis, V34, pp. 1076-1084, 2013.

Sonnenberg, A. et al. "Dielectrophoretic Isolation of DNA and Nanoparticles from Blood", Electrophoresis V33, 2482-90, 2012.

Sosnowski, R. et al. "Active Microelectronic Array System for DNA Hybridization, Genotyping and Pharmacogenomic Applications", Psychiatric Genetics 2002, 12:181-192.

Sosnowski, R. et al. "Rapid Determination of Single Base Mismatch in DNA Hybrids by Direct electric Field Control", Proc. Nat Acad. Sci. USA, vol. 94, pp. 1119-1123, 1997.

Sukhorukov, V.L. et al. "A single-shell model for biological cells extended to account for the dielectric anisotropy of the plasma membrane", Journal of Electrostatics, vol. 50, No. 3, pp. 191-204, Feb. 2001.

Sun, M. et al. "Continuous on-chip cell separation based on conductivity-induced dielectrophoresis with 3D self-assembled ionic liquid electrodes", Analytical Chemistry, vol. 88, No. 16, pp. 8264-8271, Aug. 2016.

Tsikritsis, D. et al. "Label-free biomarkers of human embryonic stem cell differentiation to hepatocytes", Cytometry, vol. 89, No. 6, pp. 575-584, May 2016.

Vitagliano, V. et al. "Diffusion coefficients for aqueous solutions of sodium chloride and barium chloride", Journal of the American Chemical Society, vol. 78, No. 8, pp. 1549-1552, 1956.

Wei, C. et al. "From bench to bedside: successful translational nanomedicine: Highlights of the Third Annual Meeting of the American Academy of Nanomedicine", Nanomedicine: Nanotechnology, Biology and Medicine, V3, Issue 4, pp. 322-331, Dec. 2007.

(56) References Cited

OTHER PUBLICATIONS

Wei, X.F. et al. "Impedance characteristics of deep brain stimulation electrodes in vitro and in vivo", J. Neural Eng., vol. 6, No. 4, p. 046 008, Jul. 2009.

Weng, P.Y. et al. "Size-dependent dielectrophoretic crossover frequency of spherical particles", Biomicrofluidics, vol. 10, No. 1, p. 011 909, Jan. 2016.

Yang, X. et al. "Integrated separation of blood plasma from whole blood for micro fluidic paper-based analytical devices", Lab Chip, vol. 12, No. 2, pp. 274-280, 2012.

Zhou, D. et al. "Electrochemistry in neural stimulation by biomedical implants", Electrochemistry, vol. 17, No. 3, pp. 249-262, 2011.

ELECTROKINETIC MICROELECTRODE DEVICES AND METHODS FOR BIOMARKER ANALYSIS

CROSS-REFERENCE TO RELATED APPLICATIONS

This patent document is a U.S.C. § 371 National Stage application of International Application No. PCT/US2020/047519 entitled "ELECTROKINETIC MICROELECTRODE DEVICES AND METHODS FOR BIOMARKER ANALYSIS" filed on Aug. 21, 2020 which further claims priority to and benefits of U.S. Provisional Patent Application No. 62/891,204 entitled "ELECTROKINETIC MICROELECTRODE DEVICES AND METHODS FOR BIOMARKER ANALYSIS" filed on Aug. 23, 2019. The entire contents of the aforementioned patent applications are incorporated by reference as part of the disclosure of this patent document.

TECHNICAL FIELD

This patent document relates to analyte sensors.

BACKGROUND

Dielectrophoresis (DEP) is an electrokinetic phenomenon in which a force is exerted on a dielectric particle (e.g., polarizable particle, including molecules and nanoscale particles) in a suspending medium when the particle is subjected to a non-uniform electric field. Dielectrophoresis can be used to attract and separate various particles in aqueous media, depending on the dielectric response of the particle in the presence of the non-uniform electric field. Although particles in general can exhibit dielectrophoretic activity in the presence of an electric field, the magnitude of the dielectrophoretic force depends on the type of medium, certain properties of specific particles, e.g., electrical properties and shape and size, and the frequency of the electric field exerted on the particles.

SUMMARY

Disclosed are miniaturized electronic systems, devices and methods for biomarker analysis, which can be incorporated into blood collection tubes and other containers that enable the immediate isolation, concentration, analysis and storage of disease related biomarkers upon blood draw. The miniaturized electronic systems can become activated and immediately carry out in-situ sample preparation, processing and storage of biomarkers for later down-stream analysis in the clinical laboratory or other settings. Such systems are able to carry out in-situ detection, identification and analysis of specific biomarkers and other entities that require more immediate results.

In some embodiments, the miniaturized electronic systems include a specially designed high surface area folded or sandwiched electrokinetic microelectrode arrays (also called microarrays, chips, or devices) that allows both AC dielectrophoretic (DEP) and DC electrophoretic based separation and isolation and other processes to be used for the concentration and storage of the biomarkers.

In some embodiments, an electronic device for biomarker analysis in a biofluid includes an electrokinetic microelectrode array chip operable to separate and isolate a biomarker in a biofluid using one or both of AC dielectrophoretic (DEP) and DC electrophoretic based forces, the electrokinetic microelectrode array chip including: a support structure, an array of microelectrodes coupled to a first side of the support structure, a permeation layer at least partially formed on the array of microelectrodes over the support structure, and one or more detectors, sensors, and/or emitters coupled to a second side of the support structure, wherein the electrokinetic microelectrode array chip includes a folded or a sandwiched configuration of the array of microelectrodes on the first side of the support structure and the one or more detectors, sensors, emitters, or combination thereof on the second side of the support structure that forms a microfluidic channel, and wherein the electrokinetic microelectrode array chip device is able to be incorporated within a container to hold the biofluid.

In some embodiments, a method of analyzing one or more biomarkers in a biofluid includes obtaining a biofluid from a subject, wherein the biofluid is placed in a collection tube including an electrokinetic microelectrode array including a support structure, an array of microelectrodes coupled to a first side of the support structure, a permeation layer at least partially formed on the array of microelectrodes over the support structure, and one or more detectors, sensors, and/or emitters coupled to a second side of the support structure, wherein the electrokinetic microelectrode array includes a folded or a sandwiched configuration of the array of microelectrodes on the first side of the support structure and the one or more detectors, sensors, emitters, or combination thereof on the second side of the support structure that forms a microfluidic channel; contacting the biofluid with the electrokinetic microelectrode array to separate and isolate the one or more biomarkers in the electrokinetic microelectrode array, wherein the electrokinetic microelectrode array separates and isolates the one or more biomarker(s) from the biofluid using one or both of AC dielectrophoretic (DEP) and DC electrophoretic based forces; and analyzing the one or more biomarkers in the biofluid.

The subject matter described in this patent document can be implemented in specific ways that provide one or more of the following features.

DETAILED DESCRIPTION

Figure 1:
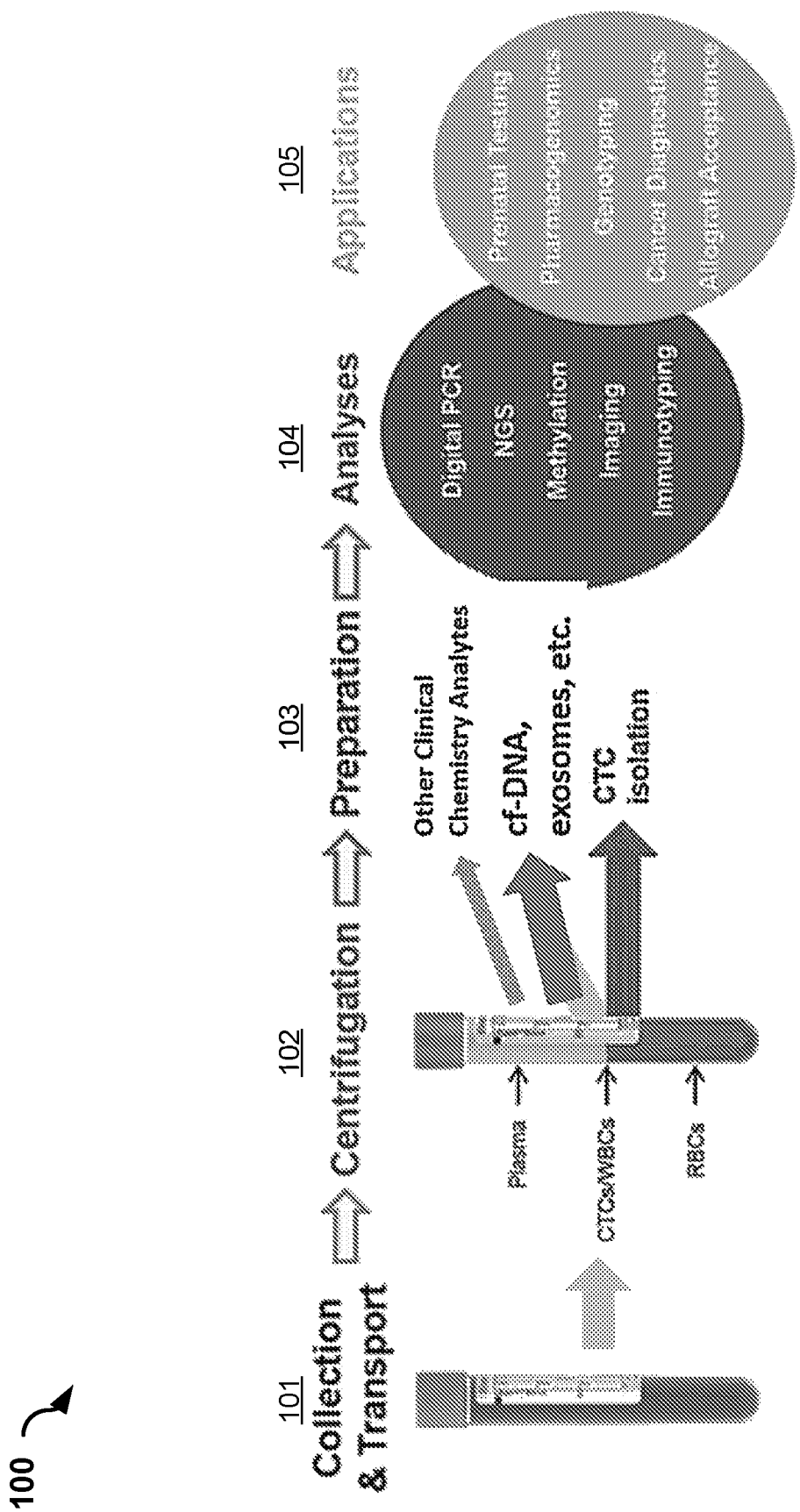
FIG. 1 shows a diagram illustrating a conventional technique or present pathway for blood biomarkers going to the clinical laboratory for molecular diagnostic and clinical chemistry analyses.

The increasing interest in molecular diagnostics for research or clinical applications, e.g., forms of personalized or precision medicine, is concomitant with the rapid improvements in sequencing technologies and amplification techniques. This progress puts greater burden on sample preparation, throughput, yield, and maintaining sample integrity. Yet little has changed with fundamental techniques and best practices in a several decades. Dielectrophoretic separations offer tremendous benefits over more traditional techniques, and hold promise to positively affect these critical metrics.

Disclosed are miniaturized electronic systems, devices and methods for biomarker analysis, which can be incorporated into blood collection tubes and other containers that enable the immediate isolation, concentration, analysis and storage of disease related biomarkers upon blood draw. The miniaturized electronic systems can become activated and immediately carry out in-situ sample preparation, processing and storage of biomarkers for later down-stream analysis in the clinical laboratory or other settings. Such systems are able to carry out in-situ detection, identification and analysis of specific biomarkers and other entities that require more immediate results. Furthermore, the disclosed systems, devices and methods immediately overcome many of the problems related blood draw logistics, including blood degradation and biomarker degradation due to delay in processing, storage and many other adverse effects that occur before the blood is actually analyzed.

In some embodiments, the miniaturized electronic systems include a specially designed high surface area folded or sandwiched electrokinetic microelectrode array (e.g., microarray) chip device that allows both AC dielectrophoretic (DEP) and DC electrophoretic based separation and isolation and other processes to be used for the concentration and storage of the biomarkers.

In some embodiments, the miniaturized electronic systems can be incorporated into a detection-sensor chip that is flip-chip bonded to the electrokinetic chip. This chip incorporates uv/vis light emitters, detectors and other sensors that allow more immediate analysis of certain specific biomarkers and other blood constituents. Other components of the miniaturized system can include a control unit with frequency generator and RF transmitter; a battery power unit; micro-pumps and control valves; and/or buffer and reagents reservoirs.

In some implementations, the disclosed systems and devices are designed to isolate for storage and/or analysis a wide range of disease related biomarkers that can include, but are not limited to cell free (cf) DNA, RNA, nucleosomes, exosomes, extracellular vesicle (EVs), drug delivery nanoparticles, cell organelles (mitochondria, etc.) proteins/enzymes, protein complexes, virus, bacteria, cancer cells and other important analytes and entities.

In addition to blood draw tubes, blood collection bags and other blood storage containers, the example devices can be incorporated or simply added (dropped into) urine collection tubes, and other collection tubes and containers used for clinical, biological and research applications, for example. In addition to undiluted blood, the example systems and devices can also be operated in other high conductance solutions ~0.5 to 1.5 Siemens/m (S/m) including but not limited to: buffy coat blood, plasma, serum, urine, saliva, cerebrospinal fluid (CSF), and other biological fluids, buffers and environmental samples.

Conventional blood draw logistics and techniques for collecting, storage and transport of blood can create problems for later down-stream biomarker analysis in the clinical lab setting. This is true for many molecular diagnostic biomarkers such as cf-DNA, RNA, exosomes, cancer cells, and other entities that are labile and present in only very low amounts. In these cases, blood processing and extended delay or storage of the blood can lead to biomarker loss and the release of blood cell components that later interfere with analysis of the desired biomarkers. Even, temporary cooling of the blood may have adverse effects. Also, choices of blood draw tubes must be made regarding whether the tubes contain additives such as heparin, EDTA, etc., used for the downstream preparation of plasma or serum. These additives are often incompatible with many of the different biomarkers that are to be later analyzed.

The disclosed systems, devices and methods address these problems and provide unique solutions. For example, in some implementations of the example miniaturized electronics system including the electrokinetic microelectrode array chip device, the system immediately upon blood draw collects, concentrates, and stores all the desired biomarkers "in-situ," on the electrokinetic microarray device surface. As a result, the biomarkers are now both protected and prevented from being further degraded, mixed and diluted with the numerous interfering substances that are released by red and white blood cell lysis and other ongoing cellular and biochemical/enzymatic processes—challenges often associated with conventional blood draw and analysis techniques.

In comparison, for example, while some existing techniques, such as adding RNAse inhibitors to the blood, can help prevent RNA degradation, they do nothing to prevent release of relatively large amounts of other RNA from white blood cells which begin to lyse soon after blood collection. Release of these competing biomolecules makes subsequent analysis of specific disease related RNA's much more difficult. The immediate isolation of the molecular biological biomarkers also assures that whatever additive is being used in the blood tube will have only negligible effects on the biomarkers being collected and stored inside the system.

The disclosed systems, devices and methods are also capable of carrying out the more immediate analysis of certain specific biomarkers. By way of just one example, the immediate measurement and reporting of the cf-DNA level in the blood is valuable as this often indicates that serious pathology or other problems exists. The disclosed systems, devices and methods can be implemented in un-diluted blood and other high conductance sample solutions, which is another major advantage over conventional techniques.

The disclosed systems, devices, and method are also capable of carrying out direct separation and analysis of targeted biomarkers with a blood sample without the need to go through centrifugation, chemical isolation, and precipitation steps associated with conventional techniques. For example, in some implementations, the miniaturized electronics system including the electrokinetic microelectrode array chip device can be added directly to a tube containing a blood sample. The disclosed systems, devices, and method are then able to carry out a rapid analysis of the biomarkers in the blood sample without degradation of the blood.

The disclosed systems, devices, and method are also capable of carrying out direct separation and analysis of targeted biomarkers from a single blood sample. Conventional techniques often require obtaining one blood sample for each test to be performed on the sample. This requires multiple blood draws from the patient, resulting in a more arduous and time extensive process. The disclosed systems, devices, and method enable performing multiple tests on a single blood sample drawn from the patient.

Example embodiments and implementations of the miniaturized electronic systems and electrokinetic microelectrode array chip device are disclosed below.

It is well understood that the blood draw process for collecting, storage and transport of blood can frequently cause problems for later down-stream biomarker analysis in the clinical lab setting. This is true for many molecular diagnostic biomarkers (e.g., cf-DNA, RNA, exosomes, cancer cells, etc.) that are often labile and present in only very low amounts. In these cases, blood processing and extended delay can lead to biomarker loss and the release of blood cell components that later interfere with analysis of the desired biomarkers. Also, choices of blood draw tubes must be made regarding whether the tubes contain, heparin, EDTA, or other additives which are often not compatible with one or more of the many different biomarkers that are later to be detected and analyzed.

FIG. 1 shows a diagram illustrating a process 100 of a conventional technique used for obtaining blood biomarkers to be sent to the clinical laboratory for molecular diagnostic and clinical chemistry analyses. The process 100 includes an initial Step 101 of collecting and transporting the blood sample. After collection and transport, the sample is centrifuged in Step 102, separating the sample into three layers: plasma (top layer), white blood cells (WBCs) and circulating tumor cells (CTCs) (middle layer), and red blood cells (bottom layer). Each of the three layers are then prepared for separation and analysis of the individual constituents comprised in each layer (e.g., clinical chemistry analytes, cf-DNA, exosomes, and CTC isolation). In Step 103, the prepared samples can then be analyzed using an array of different techniques to include digital polymerase chain reaction (PCR), next generation sequencing (NGS), methylation, imaging, and immunotyping. Lastly, the process 100 includes a Step 105, where the samples can be used for a variety of applications to include prenatal testing, pharmacogenomics, genotyping, cancer diagnostics, and allograft acceptance. However, in using the process 100, from the time of the blood draw, samples can experience degradation and the loss of important biomarkers during temporary storage and the time required for shipment and later preparation of plasma, serum and for specific cell isolation.

The example miniaturized electronic systems is envisioned to overcome many of the blood draw problems and logistics that occur in the collecting and storage of blood before later down-stream biomarker analysis in the clinical lab. The example miniaturized electronic allows for direct separation of targeted biomarkers without the need to go through centrifugation, chemical isolation, and precipitation steps often required using conventional techniques for analyzing biomarkers.

Figure 2:
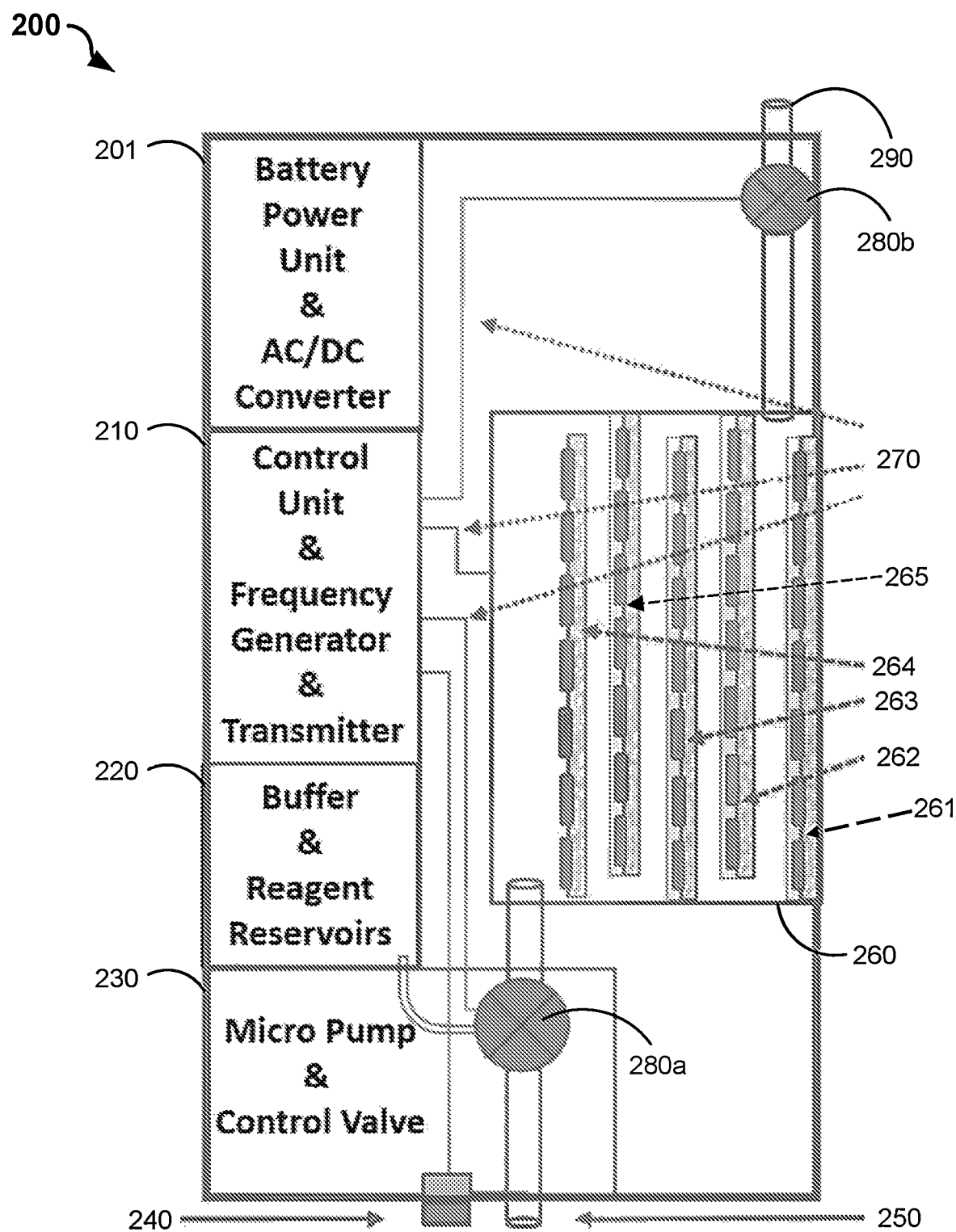
FIG. 2 shows a diagram illustrating an example embodiment of a miniaturized electronic system in accordance with the present technology.

FIG. 2 shows a diagram illustrating an example embodiment of a miniaturized electronic system 200 in accordance with the present technology. Example features and components of the example miniaturized electronic system 200 includes a specially designed high surface area folded or sandwiched electrokinetic microelectrode array device 260 that allows both AC dielectrophoretic (DEP) and DC electrophoretic based separation and isolation and other processes to be used for the concentration and storage of the biomarkers.

In some embodiments, the electrokinetic microelectrode array device 260 includes a support structure, an array of microelectrodes coupled to a first side of the support structure, a permeation layer at least partially formed on the array of microelectrodes over the support structure, and one or more detectors, sensors, and/or emitters coupled to a second side of the support structure. In some implementations, the electrokinetic microelectrode array device 260 includes a folded or a sandwiched configuration of the array of microelectrodes, which are labeled in FIG. 2 as 261, 262, 263, 264, and 265 on the first side of the support structure and the one or more detectors, sensors, emitters, or combination thereof on the second side of the support structure that forms a microfluidic channel.

In some example embodiments of the electrokinetic microelectrode array device 260, like that shown in FIG. 2, the device 260 can be configured as a flip-chip bonded to a second key component, which is a detection-sensor chip device that allows in-situ detection and analysis of the biomarkers that are collected and stored on the surface of the electrokinetic chip, as well as other analytes still in the blood itself.

The electrokinetic microelectrode array device 260 can be configured with other components of the miniaturized electronic system 200. As shown in FIG. 2, the blood sample including the target biomarkers is drawn into the inlet port 250 by the micropump & control valve unit 230. Once drawn into the inlet port 250 controlled by the inlet control valve 280a, a fluidic sensor 240 is activated, signaling the introduction of the blood into the miniaturized electronic system 200. The blood sample including the targeted biomarkers then travels through the inlet port 250 and flows over the electrokinetic electrode array chip device 260. The blood passes over the electrokinetic electrode array chip device 260, while the biomarkers remain, isolated on the surface of the electrokinetic electrode array chip device 260. After passing over the electrokinetic electrode array chip device 260, the blood exits the miniaturized electronic system 200 through the outlet port 290 controlled by outlet control valve 280b. The miniaturized electronic system 200 can now flow from the buffer and reagent reservoirs 220, a stabilizing buffer onto the electrokinetic electrode array chip device 260 containing the isolated biomarkers. The miniaturized electronic system 200 further includes a unit 201 including a battery power unit and AC/DC converter, a unit 210 including a control unit, frequency generator, and RF transmitter that are in operative communication with the electrokinetic electrode array chip device 260.

This microarray chip device 260 allows both AC dielectrophoretic (DEP) and DC electrophoretic based separation and other processes to be used for the rapid isolation, concentration, and in-situ or on-chip storage of the biomarkers. The electrokinetic microelectrode array chip 260 is operable to isolate directly from undiluted whole blood a wide range of disease related biomarkers that can include, but are not limited to cell free (cf) DNA, RNA, nucleosomes, exosomes, extracellular vesicle (EVs), drug delivery nanoparticles, cell organelles (mitochondria, etc.) protein complexes, virus, bacteria, cancer and other cells and other important analytes and entities.

The example electrokinetic microelectrode array chip device 260 is flip-chip bonded to a detection-sensor chip device that allows in-situ detection and analysis of the biomarkers that are collected and stored on the surface of the electrokinetic chip, as well as other analytes still in the blood itself. In some embodiments, the detector-sensor chip incorporates uv/vis light emitters, mini/micro size fluorescent detectors and/or other chemical sensors that allow more immediate analysis of certain specific biomarkers and other blood constituents or conditions. This may include but is not limited to some biomarkers being isolated on the electrokinetic chip (cf-DNA, exosomes, rare cancer cells, etc.), which can be detected and/or analyzed by using of fluorescent dyes (DNA or RNA dyes, etc.) or other fluorescent based reagents (fluorescent antibodies, etc.). Other analytes in the blood that are not being isolated, but whose immediate detection and/or analyses may be desirable can include but are not limited to: glucose, pH, electrolytes, enzymes, hormones, lipids (fats), other metabolic substances, and proteins. A variety of mini/micro sensor devices, well known in the art, have been designed for these purposes. Such sensor devices can be incorporated into the detector-sensor chip device. Other components of the miniaturized systems include: a control unit with frequency generator and RF transmitter; a battery power unit; micro-pumps and control valves; and buffer and reagents reservoirs.

In some implementations, the example miniaturized electronic systems can be incorporated into blood collection tubes and other containers that enable the immediate isolation, concentration, analysis and storage of disease related biomarkers upon blood draw.

Figure 3:
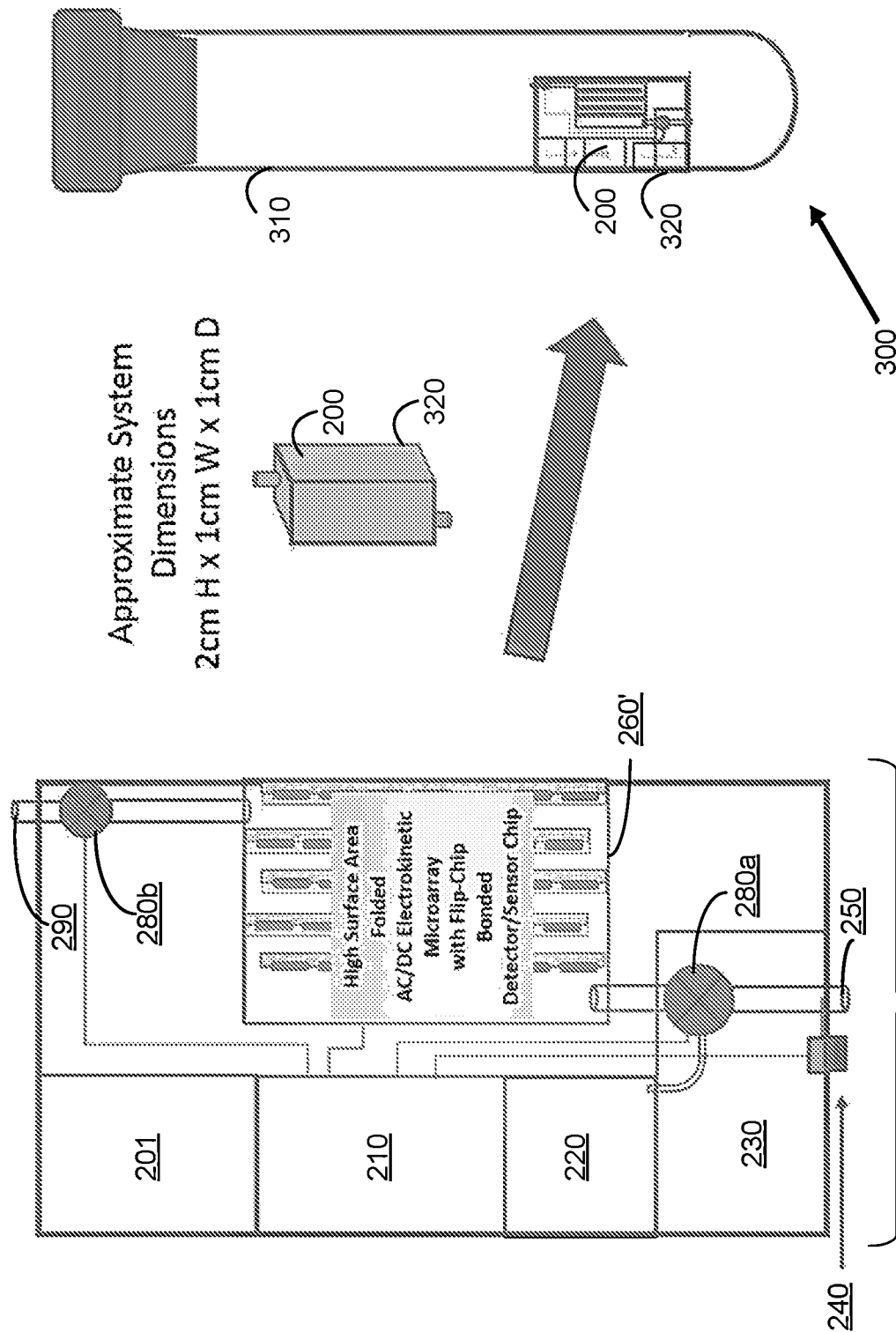
FIG. 3 shows a diagram illustrating the example miniaturized electronic system (shown in FIG. 2) being incorporated into a blood draw tube.

FIG. 3 shows a diagram illustrating the example biomarker analysis system 300 that incorporates the miniaturized electronic system 200 into a blood draw tube 310. The overall size of the systems that would be used in 1 mL to 5 mL blood draw tubes 310 would be from about 1.5 cm to 2.5 cm in height by 0.5 cm to 1.5 cm in width by 0.5 cm to 1.5 cm in depth. However, present fabrication technology would allow both smaller micro-systems to be built, as well as larger systems could easily be fabricated.

In the example shown, the miniaturized electronic system 200 is mounted/bonded inside near the bottom of the blood collection tube 310. The miniaturized electronic system 200 includes an example embodiment of the electrokinetic microelectrode array device 260 that is configured as a high-surface area folded AC/DC microarray with a flip-chip bonded detector and sensor chip, labeled as 260' in FIG. 3. The whole miniaturized electronic system 200 is encapsulated/packaged in a protective covering 320 that prevents liquid (e.g., blood) from entering the device at any other location but the input port, which have been designed for bringing the blood into the system. The miniaturized electronic system 200 is programmed via a special blood sensor to become activated and immediately carry out in-situ sample preparation, processing, analysis and storage of biomarkers for more complete down-stream analysis in the clinical laboratory or other settings.

Figure 4:
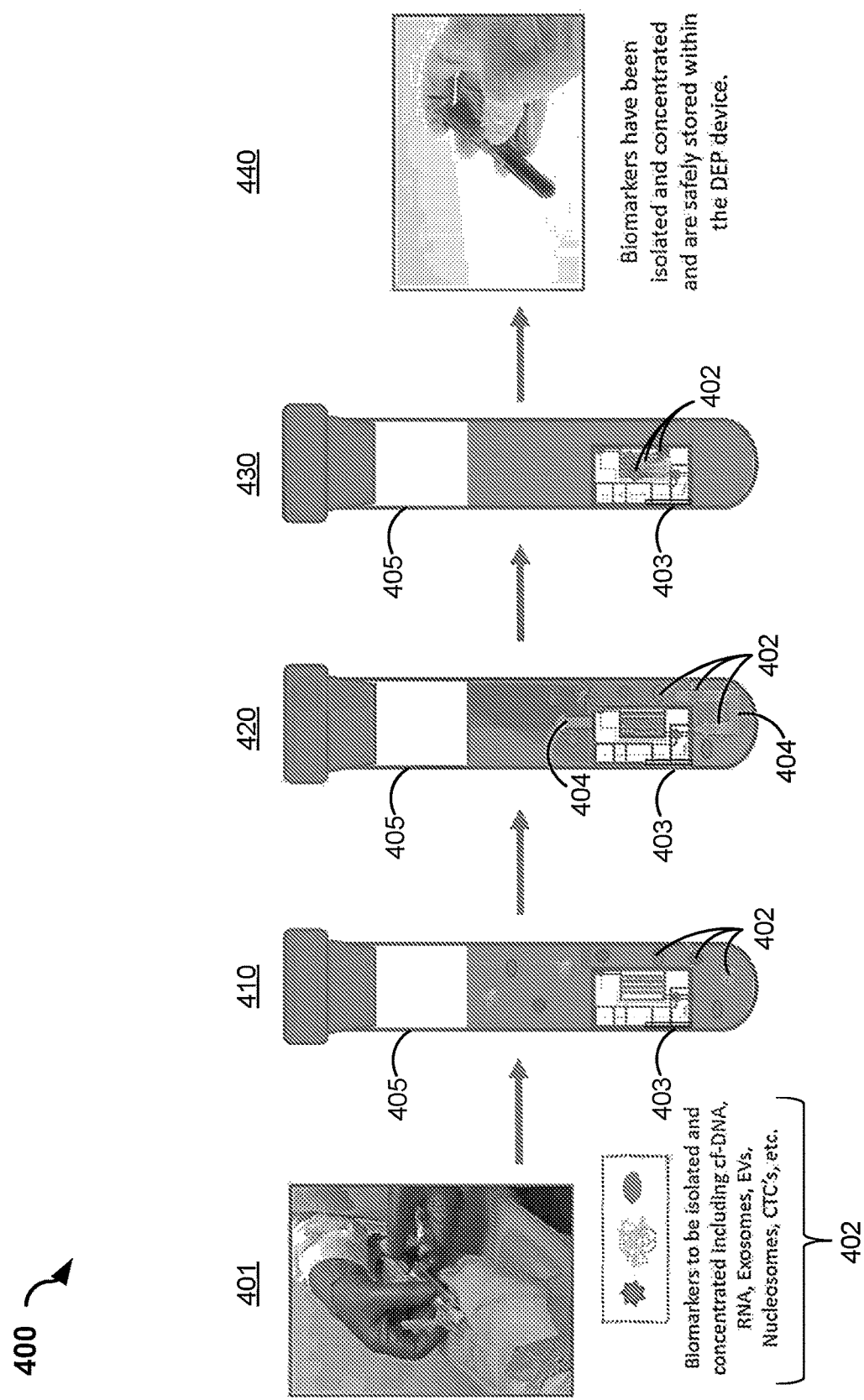
FIG. 4 shows a diagram illustrating example blood draw and biomarker isolation steps in some implementations of the example miniaturized electronic system.

FIG. 4 shows a diagram illustrating example blood draw and biomarker isolation process 400 using any of the example embodiments of the electrokinetic microelectrode array device 260 incorporated into an embodiment of the miniaturized electronic system 200, such as the example miniaturized electronic system 403 shown in FIG. 4. In the example implementation, the process 400 includes a Step 401 of drawing the blood from the user into a tube 405, where the blood contains the biomarkers 402 to be isolated (e.g., cf-DNA, RNA, exosomes, EVs, nucleosomes, CTC's, etc.). Step 410 includes the system activation when the blood sensor of the miniaturized electronic system 403 detects that the blood has been drawn. Step 420 is the collection of cf-DNA, exosomes, EVs, nucleosomes, CTC's and other biomarkers.

In Step 420 the blood is drawn into the system by the micro-pump at the inlet port as indicated by the arrows 404; the blood flows through the sandwiched AC/DC electrokinetic microelectrode array devices and exits at the outlet port. The blood can transit (e.g., flow through) the device at a rate that could range from about 1 μl/sec (60 μl/min) to 20 μl/sec (1200 μl/min). At a rate of 10 μl/sec (600 μl/min), a 1 ml blood sample could be processed in about less than two minutes.

During this transit process, the biomarkers are isolated and concentrated on the microarray surface as shown in Step 430. Generally, in the AC mode for DEP based isolation, an AC frequency in the range of from 1 kHz to 20 kHz and AC voltages in the range of about 1 V to 20 V AC are used to isolate, concentrate and firmly hold biomarkers in the range of 20 nm to 800 nm in the DEP high-field regions areas on or near the edges of the microelectrodes. AC voltages in the range of 1 volt to 50 volts could be applied, with AC voltages in the range of from 3 volts to 15 volts being more suitable. In the AC mode, the microelectrodes would be biased in checkerboard or other fashion as to create areas or regions of high field DEP and low field DEP which are suitable for collecting the various biomarkers in the sample. In the DC mode for electrophoretic isolation, a voltage of from 1 volt to 50 volts could be applied, with DC voltages in the range of from 2 volts to 20 volts being more suitable. In the DC or electrophoretic mode any of the negatively charged entities would be attracted to and collected on the positively biased electrodes. The system now pumps from the buffer reservoir, a stabilizing buffer into the chamber containing the microarrays with biomarkers concentrated on their surface.

Step 430 is the completion of the process showing that each of the biomarkers are isolated and concentrated on the microarray surface; and at Step 440 the tube 405 is now ready for storage, and/or transport to the clinical lab. If on-chip analyses of certain biomarkers is desired (e.g., pre-analyses), then the detector-sensor chip component can be activated to carry out rapid detection of the specific biomarkers.

Figure 5:
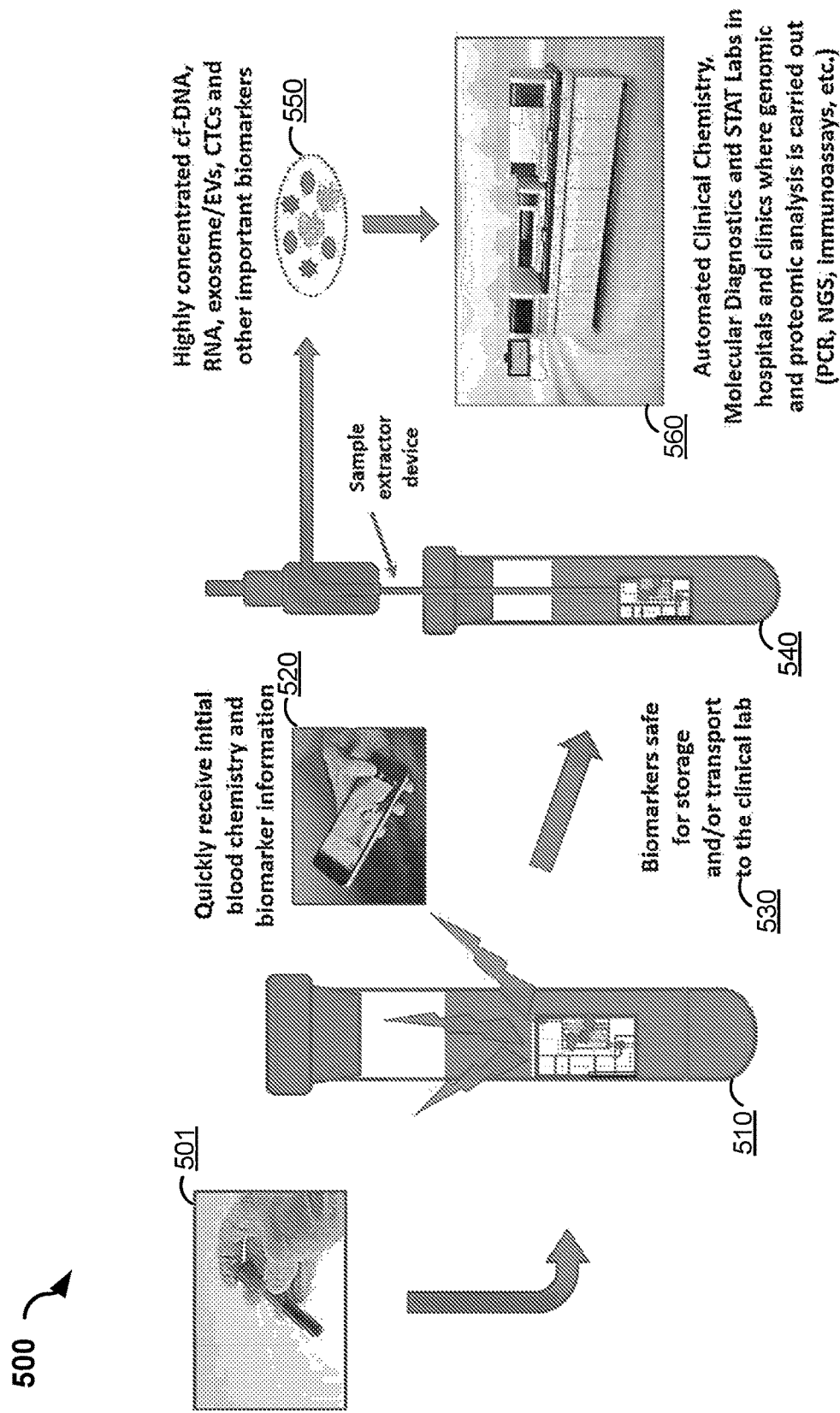
FIG. 5 shows a diagram illustrating an example of an overall method where the miniaturized electronic systems are able to carry out: (a) immediate blood processing and biomarker isolation; (b) if so desired, the rapid in-situ/on-chip detection, identification and analysis of certain specific biomarkers collected on the electrokinetic microarray surface, as well analytes in the blood is carried out; (c) the reporting via RF or other transmitting device of the on-chip analysis results; (d) the protection and storage of the concentrated biomarkers for transport; and (e) the final release of the biomarkers into the clinical laboratory system or other diagnostic systems for more complete final analysis.

FIG. 5 shows a diagram illustrating an example of the overall process 500 where the miniaturized electronic systems are able to carry out: (a) immediate blood processing and biomarker isolation (Step 501); (b) if so desired, the rapid in-situ/on-chip detection, identification and analysis of certain specific biomarkers collected on the electrokinetic microarray surface, as well analytes in the blood is carried out (Step 510); (c) the reporting via RF or other transmitting device of the on-chip analysis results (Step 520); (d) the protection and storage of the concentrated biomarkers for transport (Step 530); and (e) the final release of the biomarkers into the clinical laboratory system or other diagnostic systems for more complete final analysis (Steps 540-560). Such final molecular diagnostic analyses can include but are not limited to immunofluorescent detection of exosome and other protein biomarkers, various PCR assays, RT PCR analysis of RNA, DNA sequencing and epigenetic analyses, DNA genotyping and many other types of biomarker and specific cell analyses.

In the example implementation, process 500 includes a Step 501 in which a tube containing the blood is obtained and ready for immediate blood processing and biomarker isolation. A miniaturized electronic system is then added directly to the blood tube. If desired, the process 500 further includes a Step 510 where a rapid in-situ/on-chip detection, identification and analysis of certain specific biomarkers collected on the electrokinetic microarray surface, as well analytes in the blood is carried out. In Step 520, results from the on-chip analysis in Step 510 can be quickly reported and/or received via an RF signal (e.g., to a cellular device) to a user, providing initial blood chemistry and biomarker information. The process 500 includes a Step 530 where the concentrated biomarkers are safely stored and prepared for transport to the clinical lab for further analysis. After transportation to the clinical lab, the process includes a Step 540 in which the concentrated biomarkers are removed from the tube via a sample extraction device. In Step 550, the concentrated biomarkers are then transferred to a clinical laboratory system or other diagnostic systems for more complete final analysis in Step 560.

In addition to blood draw tubes, blood collection bags and other blood storage containers, the example devices of the disclosed technology can be incorporated or simply added (e.g., dropped into) into urine collection tubes, and other collection tubes and containers used for clinical, biological and research applications. Also, in addition to undiluted blood, the systems and devices in accordance with embodiments of the disclosed technology can be operated in other high conductance solution ~0.5 to 1.5 Siemens/m (S/m) as well as lower conductance solutions <0.5 S/m. Other types of sample solutions include but not limited to: buffy coat blood, plasma, serum, urine, saliva, CSF, and other biological fluids, buffers and environmental samples.

The example embodiments of methods, systems and device are envisioned to enable isolation and concentration, in-situ or on-chip sample preparation and processing, detection, identification, analysis and storage of important biomarkers. To enable these advantages and properties, the AC/DC electrokinetic microelectrode array chip component can include folded or sandwich chip structures with provide an overall larger surface area to improve the performance of the system and enable isolation of relatively larger amounts of the biomarkers that would be present in the more common one to five milliliter blood draw tubes. The folded/sandwiched structures can be designed with from five to ten or more 1 cm by 1.5 cm electrokinetic microarrays/detector-sensor chips sandwiched together within the system.

Figure 6A:
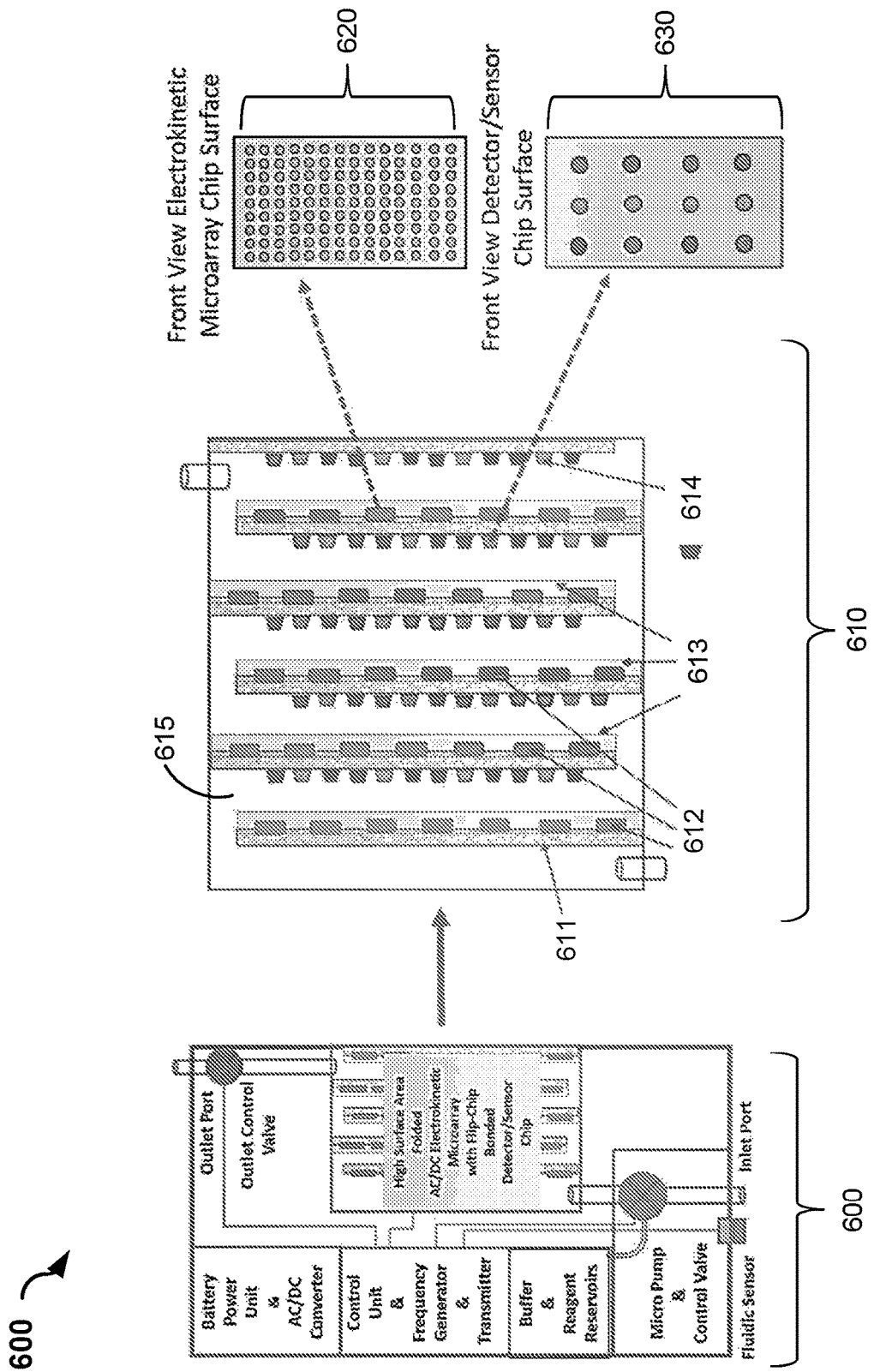
FIGS. 6A and 6B show a diagram illustrating an enlarged view of the example embodiment of the sandwiched electrokinetic microarray chip & detector-sensor chip.
Figure 6B:
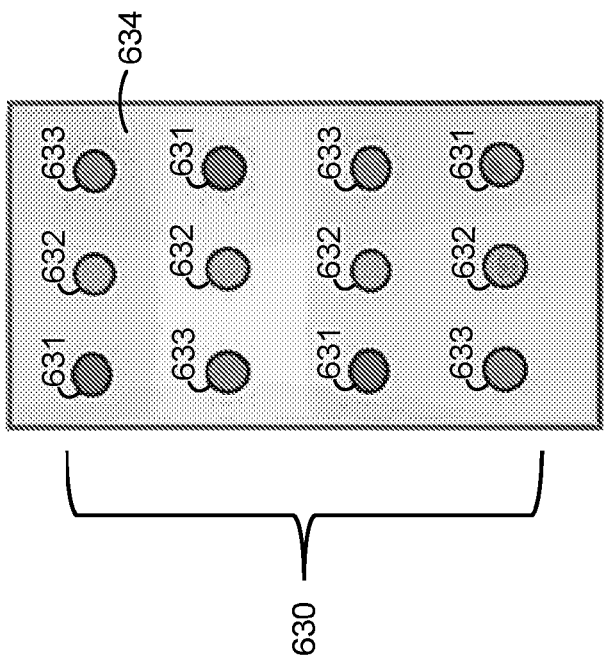
Figure 6B:
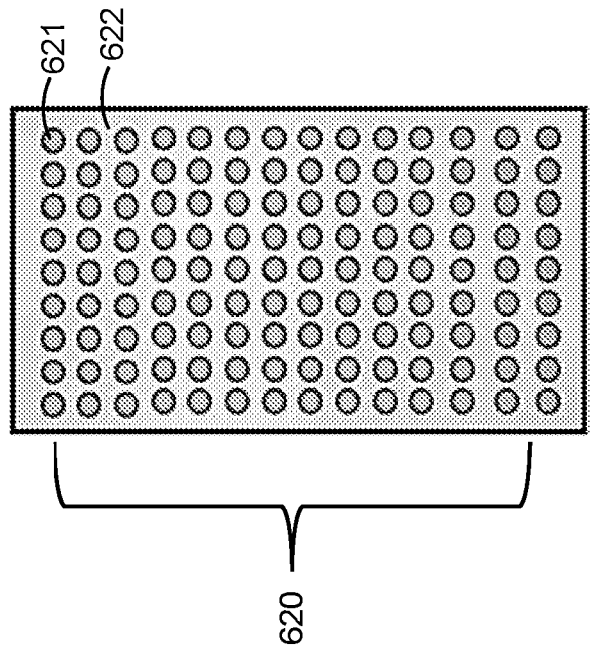
Figure 6C:
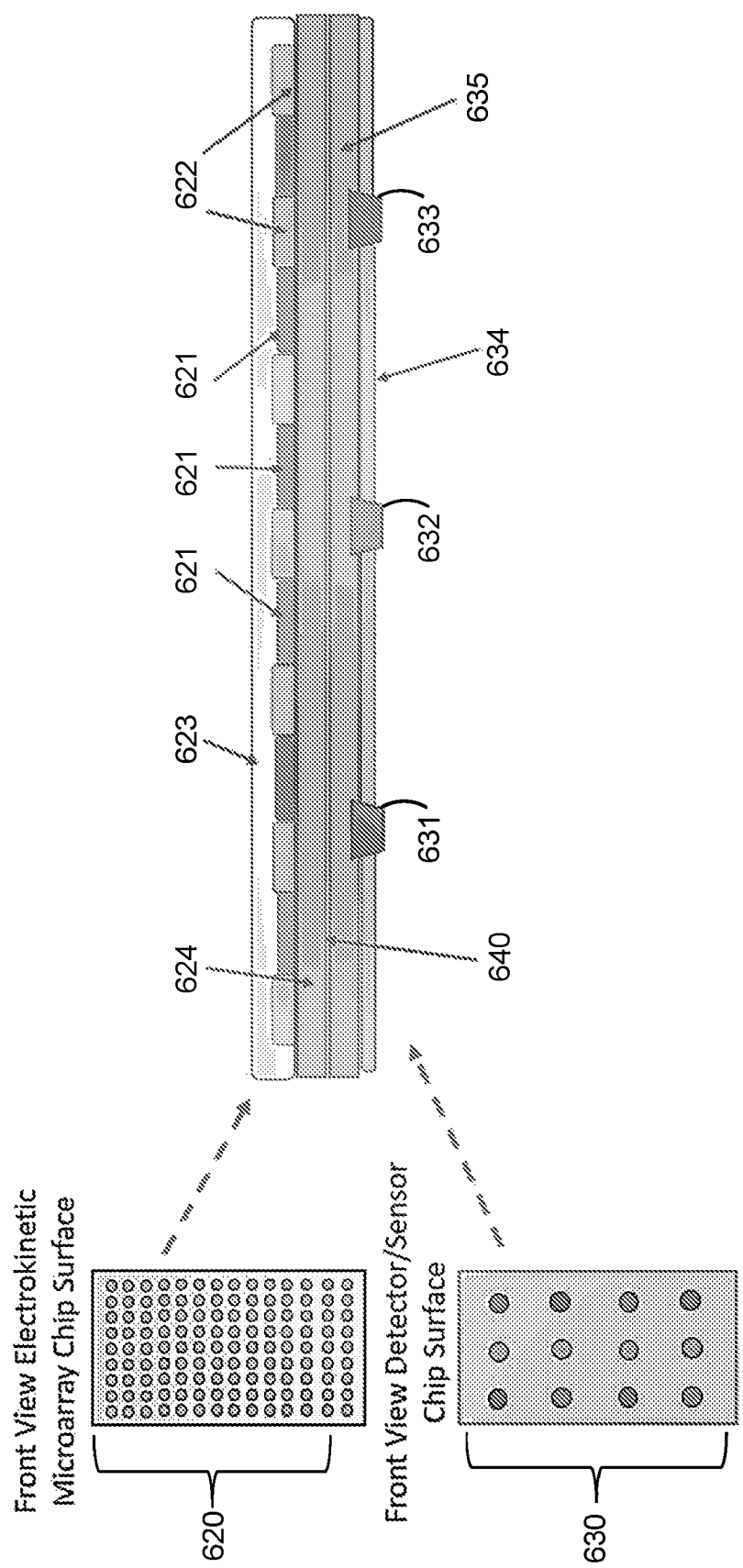
FIG. 6C shows a diagram illustrating detail of features and components of the example electrokinetic microarray chip and detector-sensor chip.

FIGS. 6A-6C show diagrams illustrating an enlarged view of an example embodiment of a sandwiched electrokinetic microarray chip & detector-sensor chip 610 in accordance with example embodiments of the electrokinetic microelectrode array device 206. As shown in FIG. 6A, the example sandwiched electrokinetic microarray chip & detector-sensor chip 610 is included in a miniaturized electronic system 600 in accordance with example embodiments of the miniaturized electronic system 200. The example AC/DC electrokinetic microelectrode array chip & detector-sensor chip 610 includes both an electrokinetic microarray chip 620 and a detector-sensor chip 630. The sandwiched electrokinetic microarray chip & detector-sensor chip 610 can include features with folded or sandwich electrokinetic microarray chips 620 and a detector-sensor chips 630, where the folded or sandwiched structure provides an overall larger surface area to improve the performance of the miniaturized electronic system 600 and enables isolation of relatively larger amounts of the biomarkers that would be present in the more common one to five milliliter blood draw tubes. The blood sample travels through the channels formed by the folded or sandwich electrokinetic microarray chips 620 and a detector-sensor chips 630. In some implementations, the channels 615 are about 0.2 mm to 0.3 mm wide.

The folded or sandwiched structures can be designed with from five to ten or more 1 cm by 1.5 cm electrokinetic microarrays chips 620 and detector-sensor chips 630 sandwiched together within the miniaturized electronic system 600. The electrokinetic microarrays chips 620 and detector-sensor chips 630 are fabricated on a substrate 611 (e.g., a silicon substrate). The detector-sensor chip 630 incorporates one or more of uv/vis light emitter(s), mini/micro size fluorescent detector(s) and other chemical sensor(s) labeled as 614 that allow more immediate analysis of certain specific biomarkers and other blood constituents or conditions. The electrokinetic microarrays chips 620 incorporates one or more electrode(s) 612. In some implementations the one or more electrode(s) 612 can include a noble metal such as platinum (Pt), gold (Au), and/or palladium (Pd). In some implementations, the one or more electrode(s) 612 is a carbon (C) electrode. FIG. 6A shows that the one or more electrode(s) 612 is encapsulated by a permeation or porous layer 613. The permeation or porous layer 613 ameliorates the adverse effects of electrolysis products formed during the biomarker collection and storage process. To prevent the targeted biomarkers from directly contacting the one or more electrode(s) 612 (and formed electrolysis products), the permeation or porous layer 613 creates a barrier that prevents the biomarkers from reaching the surface of the one or more electrode(s) 612. While barrier prevents the biomarkers from diffusing to the surface of one or more electrode(s) 612, the porous nature of the porous or permeation layer 613 enables the movement of electrolytes to and from the surface of the one or more electrode(s) 612.

Enlarged front views of the AC/DC electrokinetic chip 620 and the detector-sensor chip 630 are also shown in FIG. 6B. As shown in FIG. 6B, the electrokinetic microarray chip 620 surface includes a plurality of electrodes 621 fabricated on a substrate 622 (Shown in FIG. 6A, labeled as one or more electrode(s) 612 and substrate 611). The detector-sensor chip 630 includes detector sensors 631, UV-VIS emitters 632, and fluorescent detector and other sensors 633 also fabricated on a substrate 634, which allows for more immediate analysis of certain specific biomarkers and other blood constituents or conditions.

If desired, both smaller and larger microarrays can be fabricated for other applications. For example, in some embodiments, each electrokinetic microarray can contain anywhere from 100 to 1000 microelectrodes. The microelectrodes could range in size from 10 μm (microns) to 100 μm (microns), with center to center spacing of from 30 μm (microns) to 500 μm (microns). In some implementations, for example, the microelectrodes are circular in shape, but other shapes (e.g., oval, square, rectangular, triangular or other) may be used for certain applications. However, both electrode sizes and spacing could be smaller <10 μm and larger >100 μm if desired for other applications. The spacing between the sandwiched electrokinetic/detector-sensor microarrays could range from about 0.1 mm to 1 mm, with about 0.2 mm to 0.3 mm spacing being more optimal for blood flow from one section into the next section. By way example, the size of each of the sandwiched electrokinetic/detector-sensor microarrays could be approximately 1.5 cm high by 0.5 cm wide by 0.5 mm in thickness.

In some implementations, the microelectrode array and the sensor array can be fabricated by photolithographic methods on a silicon base or other support material (e.g., glass, plastic, ceramic, etc.), resulting in an electrokinetic/detector-sensor microarray that is about 100 μm (microns) to about 1.0 mm (millimeters) in thickness, preferably about 0.2 mm to about 0.5 mm. In some implementations, the permeation layer is applied later in a separate process (e.g., after the fabrication of the microelectrode array and sensor array). In some implementations, the binding/adhesions layers, insulating and dielectric (e.g., silicon dioxide, silicon nitrite) material between microelectrodes, the Pt, Au, or Pd microelectrodes and final permeation layer have a thickness between about 50 μm (microns) to about 250 μm (microns). In some implementations, the binding, dielectric layers and sensor device structures on the reverse side of the silicon base would also be about 50 μm (microns) to 100 μm (microns) or less in thickness. By way of one example, about five electrokinetic/detector-sensor microarrays (each approximately 1.5 cm high by 0.5 cm wide by 0.5 mm in thickness) sandwiched together with a spacing of 0.2 mm would be suitable for a 2 mL blood draw tube.

The overall size and total surface area from the example embodiment of the five microarrays (e.g., ~3.75 square centimeters) can provide enough capability to collect and concentrate all the desired biomarkers (e.g., cf-DNA, exosomes, etc.) from a 2 mL blood sample. In some implementations, the five sandwiched electrokinetic/detector-sensor microarrays are incorporated into the overall device with associated buffer reservoirs, battery, pumps etc. For a larger 5 mL blood draw tube, about ten to twelve electrokinetic/detector-sensor microarrays (e.g., each approximately 1.5 cm high by 0.5 cm wide by 0.5 mm in thickness) sandwiched together with a spacing of 0.2 mm is suitable. However, devices of many other sizes and shapes can be fabricated and designed to properly fit into the particular blood draw tube and effectively collect the biomarkers from the given amount of blood in the tube.

The example devices, such as that shown in FIGS. 6A-6C, show one arrangement of the sandwiched electrokinetic/detector devices to allow blood flow from the inlet port through each microarray sections and then exit via the outlet port. Different sets of the electrodes and microelectrodes on the device can be arranged in unique ways to carry out many different functions. Microelectrodes can be wired individually or in groups to form various asymmetric patterns for AC DEP type isolation of biomarkers. Microelectrode wiring designed for DC applications allows certain electrodes to biased positive while other are biased negative. Also, more sophisticated CMOS electrokinetic/detector-sensor arrays could be designed with on-chip control for each electrode being either on or off, being biased +/− and to control the AC and DC voltage and current levels. CMOS and other types of semiconductor on-chip control would also allow any microelectrode geometry or pattern to be produced on the chip surface.

FIG. 6C shows a diagram illustrating detail of features and components of the example electrokinetic microarray chip 620 and detector-sensor chip 630. The basic electrokinetic microelectrode chip 620 can be fabricated on a silicon base 624, with electrode structures 621 (e.g., Pt, Pd, Au, C, or graphite electrodes) about 20 nm to 100 μm (microns) in thickness, or more ideally, e.g., 50 nm to 500 nm. The electrodes structures 621 are insulated from one another by an insulator 622 (e.g., silicon dioxide or silicon nitride). The overall microelectrode array surface is over-coated with a porous coating 622 or permeation layer 622. Generally, this can be an agarose or polyacrylamide gel coating of from about 1 μm (microns) to 500 μm (microns) in thickness, or preferably ideally from 10 μm (microns) to 250 μm (microns) in thickness. However, other types of porous coating are acceptable providing they allow electrolyte contact with the surface of electrode structures 621, are robust and bond to the surface of the electrode structures 621 reasonably well, and can be impregnated with binding agents such as streptavidin, biotin, or other binding entities. In some implementations, the permeation layer 622 or porous layer 622 can include "lawns" of surface chemicals (i.e., layers, such as self-assembled monolayers), e.g., of polyethylene glycol and other hydrophilic polymers linked to the surface. Such lawns could also contain other polymers with amine, sulfhydryl, biotin and other groups that would allow attachment of affinity binding groups such as DNA probes and antibodies.

In some implementations the permeation layer 622 or porous layer 622 are porous, sintered or fritted glass permeation layers which would add structural stability and overall robustness not possible with conventional permeation layers. For example, ultra-thin porous glass structures from about 10 μm to 500 μm in thickness can be positioned and mounted over the microelectrodes and serves as the permeation layer 622 or porous layer 622. In some implementations, pore sizes can range from 50 nm to 50 μm, preferably ranging from 100 nm to 1 μm. Such pore sizes effectively limit or significantly impede the further transport of biomarkers to the electrochemically active microelectrode surface. In some implementations, the pore space or pore volume accounts for about 10% to 40% of the overall structure, assuring contact of the electrolyte with at least the same proportion of microelectrodes. The microporous or fritted glass is available commercially or can be created from a thin solid glass coating by treatment with hydrogen fluoride (HF) gas or liquid HF. In some implementations, the thin solid glass covering over the microelectrode array can be masked by applying a HF resistant coating (e.g., photolithographically), and then HF gas or liquid applied to etch out the pores, and followed by removal HF resistant coating.

In some implementations, permeation layer 622 or porous layer 622 are sintered glass permeation layers prepared from micron size glass or silica particles. Such sintered glass can be thermally (e.g., heat) fused to the surface of the microelectrode array and then HF treatment used to control pore size. Methods for modifying glass surfaces with other covalent binding or affinity binding entities that include but are not limited to DNA probes, antibodies, etc.

In some implementations the permeation layer 622 or porous layer 622 are porous permeation layers made from sintered quartz. Unlike glass, quartz is conductive and imparts novel semi-conductive properties up into the permeation layer itself, with the added benefit of reduced electrochemical effects.

In some examples, the electrode structures 621 are insulated from one another by an insulator 624 such as silicon dioxide or silicon nitride. The electrode structures 621 are generally deposited by sputtering process or other deposition process. However, in some implementations, robust electrodes that are resistant to degradation from electrolysis products (e.g., $H^+$, $OH^-$, $O_2$, $H_2$, free radicals, etc.) are used. Also, such electrodes can be operated at higher AC and DC voltages, for longer periods of time and in higher conductivity solutions (>0.5 S/m).

In addition to sputtering other deposition methods for Pt, Au, and Pd electrodes include but are not limited to: (1) Ebeam Evaporation; (2) Thermal Evaporation; (3) Electrodeposition (requires a strike layer, usually Titanium base layer); (4) Electroless deposition (various substrates, but generally need an adhesion promoter, e.g. Titanium, but maybe Tungsten/Molybdenum); (4) ALD, but may be excessive and too slow (useful for monolayers), same for MBE.

To ensure robust films that can withstand the corrosive electrochemical environment at the electrode interface, a continuous, smooth, defect-free surface is needed. Pt, Au, and Pd layers may be added via many different deposition methods broadly separable into physical and electrochemical. Physical vapor deposition (PVD) techniques include RF and DC sputtering; electron-beam evaporation, and thermal evaporation. Electrochemical deposition methods such as electroplating and electroless deposition on various substrates are generally lower cost, more common for larger parts, and require specific surface preparation for smaller features. Electrochemical deposition of Pt, Au, and Pd forms large grains, thus a rough surface, and may result in undesirable pinholes, albeit highly unlikely in thick films. However, thick films (e.g., >1 µm) are easily and economically achieved and the thick film has more material to corrode away before failure.

For micron-sized patterned electrodes, a lift-off technique is commonly used, where photoresist is applied and patterned before a PVD layer is applied. The photoresist is subsequently dissolved, and the metal remains only in the photoresist windows. For thicker films (e.g., >50 nm), chemical vapor deposition, molecular beam epitaxy and atomic layer deposition techniques are unfavorable due to their slow growth rate and expensive precursors. Local surface annealing can be carried out by (1) Laser annealing; or (2) Spot contact annealing (via some sort of inductive heater). Annealing is shown to increase surface roughness (as the atom mobility increases) with temperature and one increases crystallinity (so will reform into larger metallic crystals) as opposed to get smoother. However, a Pt/Ti layer above Si will form into a low impedance contact. In which case a simple rapid thermal annealing would work well. Sputtered films/evaporated films are <0.5 nm RMS roughness, which are suitable when the film's thickness is 100 nm or greater. Sputtering under elevated temperatures versus room temperature (RT) does not appear to make a major difference in roughness, and higher temperatures lead to slightly rougher surfaces. Laser annealing using laser annealers can affect the surface properties, or to rapidly anneal (e.g., lattice align) implanted dopants in semiconductors without giving them a chance to diffuse into the bulk. That said, these have heat zones on the order of 100 nm to 10 µm, depending on the purpose. In some examples, a very low dose can ensure that only the surface is melted. Yet in some cases, ablation may be a concern. Notably, a fabrication method can involve using electrochemical deposition to achieve a thick film followed by a pulsed laser surface melt to achieve greater robustness and flatness.

The overall microelectrode array surface can be overcoated with a porous coating or permeation layer 623. In some embodiments, the porous coating or permeation layer includes agarose or polyacrylamide gel coating of from about 1 µm to 1 mm. In some embodiments, the porous coating or permeation layer has a thickness about 10 µm to 50 µm. However, other types of porous coating are acceptable providing they allow electrolyte contact with the surface of the electrode structures 621, are robust and bond to the electrode surface reasonably well, and can be impregnated with binding agents such as streptavidin, biotin, etc., that allow attachment of other entities such as oligonucleotide probes, etc.

Example methods and constructs are used with electrokinetic devices that combine AC dielectrophoretic (DEP) and DC electrophoresis to first rapidly isolate and collect biomarkers from the blood onto specific electrodes, microelectrode or defined areas of a microarray chip device. Generally, depending for AC frequencies used entities in the range of from about 20 nanometer (nm) to 20 micron (µm) can be isolated when in the alternating current (AC) or DEP mode.

Figure 7:
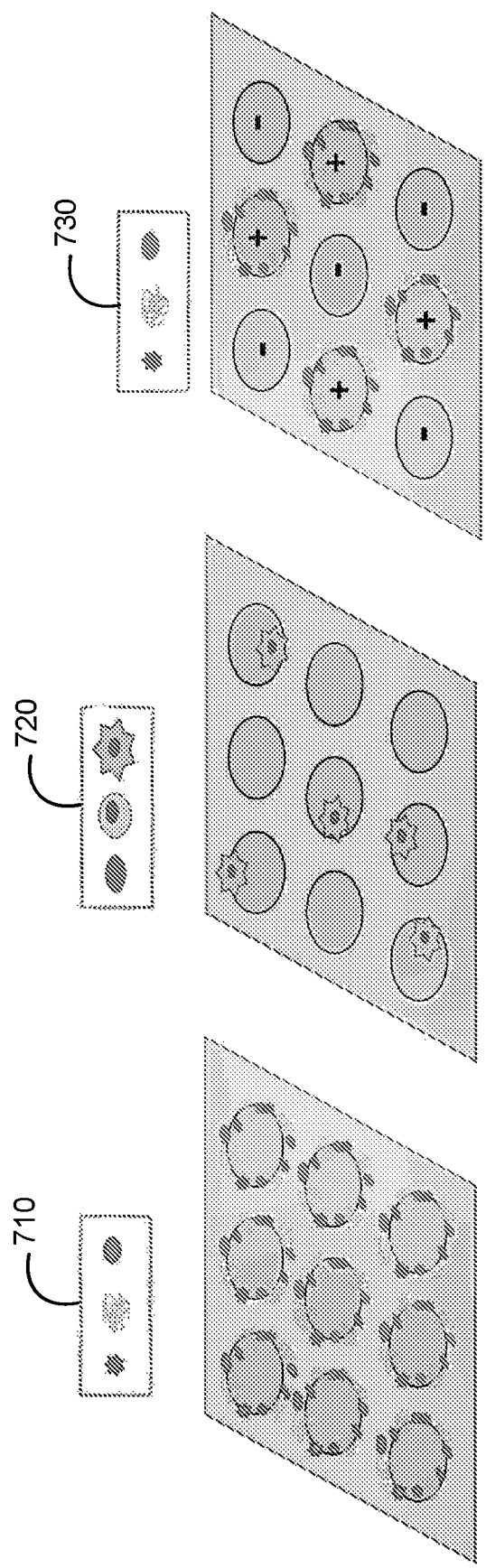
FIG. 7 shows a diagram illustrating an example implementation of the example electrokinetic microarray device.

FIG. 7 shows a diagram illustrating an example implementation of the example electrokinetic microarray device 700. In the example, the electrokinetic microarray is shown being operated at: (a) low AC frequency conditions (labeled 710); (b) high AC frequency conditions (labeled 720); and (c) under DC electrophoretic conditions (labeled 730). Under lower AC frequency conditions, biomarkers that can be isolated include cf-DNA, RNA, exosomes, EVs, and nucleosomes (labeled 710, FIG. 7). For example, in the lower AC frequency range of from about 1 kHz to 20 kHz, using voltages in the range of about 1V to 20V AC, biomarkers in the range of 20 nm to 800 nm can be moved, concentrated and firmly held in the DEP high-field regions areas on or near the edges of the microelectrodes. These would include but are not limited to high molecular weight (hmw) cell free (cf) DNA, RNA, protein aggregates, nanoparticles, exosomes, EVs, and other entities. Under these conditions, larger entities greater than 800 microns (e.g., some cells, etc.) can be attracted to the DEP low-field regions, however, modest fluid flow will remove the cells from the low-field areas and also wash away the much smaller molecules and biomolecules (panel 710, FIG. 7). Generally, entities less than about 20 nm or 10,000-20,000 MW less effected by the DEP fields. Under high AC frequency conditions, specific cells, such as rare cancer cells can be isolated from red and white blood cells in the blood sample. For example, operation at higher AC frequencies that can range from about 20 kHz to 1000 kHz and AC voltages in the range of about 1V-30V allows larger entities of about 1 µm to 20 µm in size to now be isolated onto the DEP high-field regions. Selection of specific frequencies will allow isolation of specific cells, such as cancer cells to be carried out (720, FIG. 8). Because the electrokinetic device is a folded or sandwiched structure many different separation patterns can be achieved by changing the AC frequencies and voltages/currents the individual microarrays or sections of the microarray device. By way of example, one section of the device can be run at the AC frequencies of from 1 kHz to 20 kHz that allows isolation of the biomarkers in the 20 nm to 800 nm range, while another section is operated at AC frequencies in the 20 kHz to 1000 kHz range that now allow isolation of different cell types (e.g., cancer cells) to be isolated. In addition to AC operation, the electrokinetic chip device can also be operated in the direct current (DC) mode for electrophoretic isolation of biomarkers or other entities. In this case, the biomarkers and entities are attracted by charge; negatively charged entities attracted to the positively biased microelectrodes and the positively charged entities attracted to the negatively biased electrodes; and liked charged entities are repelled form the respectively biased electrodes (730, FIG. 7). Generally, the electrophoretic process is achieved by applying a DC voltage in the range of from about 1V to 30V.

Figure 8:
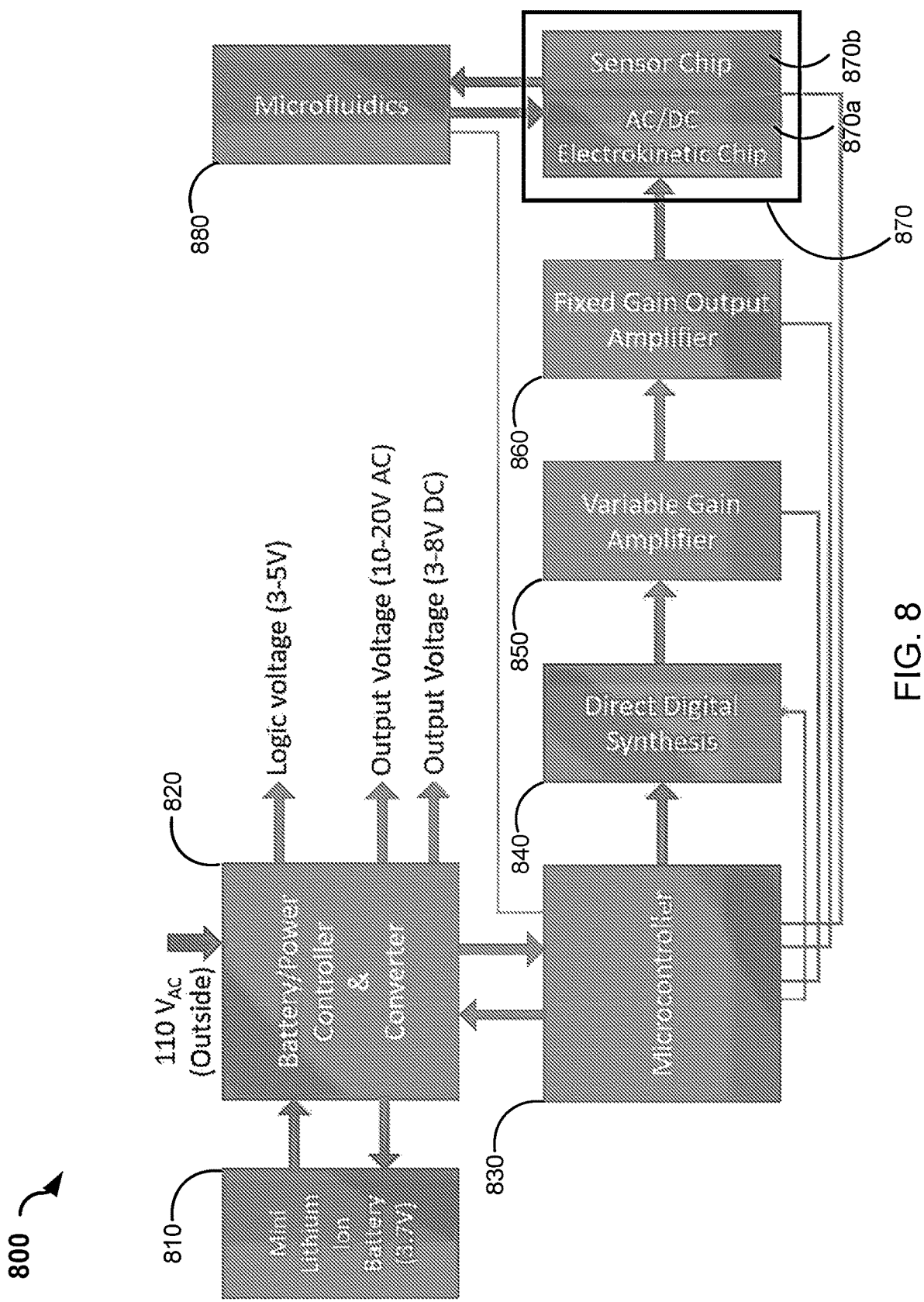
FIG. 8 shows a block diagram illustrating an example embodiment of a battery-powered device control system.

FIG. 8 shows a block diagram illustrating an example embodiment of a battery-powered device control system 800 with a microarray chip device 870, which includes an example embodiment of the electrokinetic microelectrode array (such as the microarray chip device 260, shown in FIG. 2). The microarray chip device 870 includes an AC/DC electrokinetic chip 870*a* and a sensor-detector chip 870*b*.

The battery-powered device control system 800 is powered by a miniature lithium ion battery 810 (e.g., a 3.7V lithium ion battery) that is in operative communication with a battery/power controller and converter 820 to regulate the rate at which electric current is added to or drawn from lithium ion battery 810. The battery/power controller & converter 820 is then in operative communication with a microcontroller unit 830, which directs a signal to a direct digital synthesizer 840 to produce controlled wave forms of various frequencies. The direct digital synthesizer 840 is in operative communication with a variable gain amplifier 850 that passes the signal to a fixed gain output amplifier 860. The fixed gain output amplifier is then in operative communication with the microarray chip device 870, where the biomarkers are in the blood samples pass through. In some embodiments, the example battery-powered device control system 800 includes microfluidics 880, which can comprise t the micropump & control valve unit 230, the fluidic sensor 240, and/or the buffer and reagent reservoirs 220.

In some implementations, for example, some embodiments of the electrokinetic microelectrode array device 260 can use porous membranes as mechanical filters and to create DEP high/low field regions. These can be made from conductive materials to serve as interleaved electrode layers (e.g., foil/wire mesh) and/or from insulating materials doing i-DEP. For example, applying a dielectrophoretic force through a porous media can serve as an effective filter to selecting positive-DEP particulate, even when the identically-sized particle are unable to diffuse through the media passively. This can add an additional layer of size selection and obviates concerns about capturing desired particulate within a tip.

In some implementations, for example, some embodiments of the electrokinetic microelectrode array device 260 can utilize insulation-based DEP topologies as a good match to high conductivity solutions. One can design the electrodes to be large, thus minimize local current density and its attendant corrosive effects. Electric fields may instead be constricted into large gradients in regions far away from the electrodes. Additionally, nonreactive insulating materials may be selected for the constrictive regions instead of chemically-active metals, further reducing device degradation. Constrictions in insulation-based DEP may be sufficiently distributed to ensure that any local Joule heating may be diffused over a much greater area, lowering peak temperatures and minimizing thermal gradients. Most efforts into insulator-based DEP has been focused into small devices where that require extensive lithographic patterning, which greatly limits overall active surface area and is expensive. Bulk structures, where the material itself can reliably formed into small geometries without need for patterning, allow for scaling device size over several orders of magnitudes.

Figure 9:
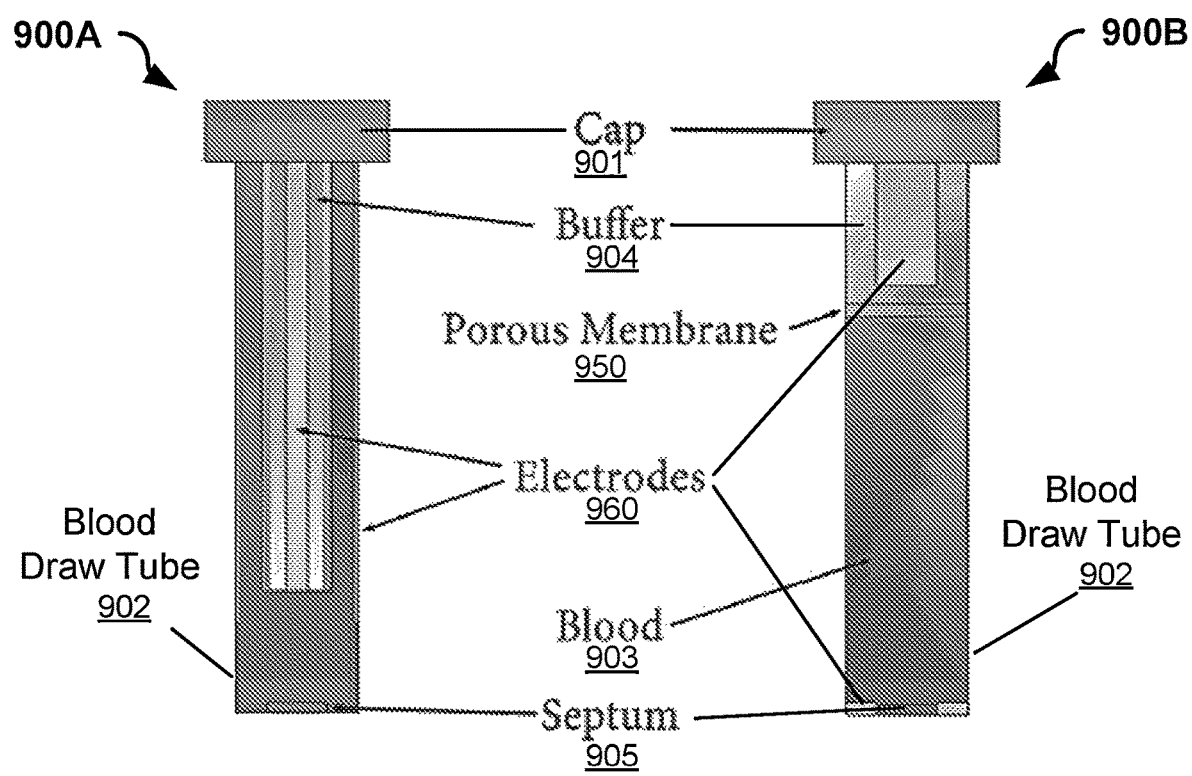
FIG. 9 shows an illustrative diagram of example embodiments of an insulator-based electrokinetic DEP microelectrode devices integrated in a blood draw tube.

FIG. 9 shows an illustrative diagram of example embodiments of an insulator-based electrokinetic DEP microelectrode devices 900A and 900B integrated in a blood draw tube 902, e.g., sealable with a cap 901 and/or a septum 905. Architecturally, both example devices 900A and 900B operate on the same principle, where a porous, open-cell, membrane 950 made of a dielectric medium is placed as to separate the blood draw tube 902 into a blood side and a buffer side. The devices 900A and 900B include electrodes 960 (e.g., such as microelectrodes) that are placed in each of the blood medium 903 and the buffer medium 904, respectively, such that the electric field applied between the electrodes 960 is locally constrained through the porous membrane 950, thus drawing positive-DEP particles to the region. Diffusion of even small particles across the barrier is extremely slow, essentially inhibiting any non-targeted transport. By applying an electric field across the membrane, local high field gradients are realized throughout the porous structures, drawing particles, e.g. cell-free DNA, RNA or exosomes, into the membrane via positive-DEP.

EXAMPLES

Some example embodiments of systems, devices and methods in accordance with the disclosed technology include the following example features, whether alone or in any combination with another or other features.

In some example embodiments, a system, device and/or method includes a high surface area folded or sandwiched AC/DC electrokinetic microelectrode array chip.

In some example embodiments, a system, device and/or method includes a high surface area folded or sandwiched AC/DC electrokinetic microelectrode array chip flip-chip bonded to a detection-sensor chip.

In some example embodiments, a system, device and/or method includes a high surface area folded or sandwiched AC/DC electrokinetic microelectrode array chip flip-chip bonded to a detection-sensor chip, that is incorporated and packaged into an electronic system for isolation of biomarkers from undiluted blood.

In some example embodiments, a system, device and/or method includes a packaged electronic system containing a high surface area folded or sandwiched AC/DC electrokinetic microelectrode array chip flip-chip bonded to a detection-sensor chip and other components that is incorporated into a blood draw collection tube.

In some example embodiments, a system, device and/or method includes a packaged electronic system containing a high surface area folded or sandwiched AC/DC electrokinetic microelectrode array chip flip-chip bonded to a detection-sensor chip and other components that is incorporated into a blood draw collection tube, that isolates, concentrates and protects biomarkers for later analysis in the clinical laboratory.

In some example embodiments, a system, device and/or method includes a packaged electronic system containing a high surface area folded or sandwiched AC/DC electrokinetic microelectrode array chip flip-chip bonded to a detection-sensor chip and other components that is incorporated into a blood draw collection tube, that isolates, concentrates and protects biomarkers, where the detector-sensor chip component can carry out more immediate detection of biomarkers.

In some example embodiments, a system, device and/or method includes a packaged electronic system containing a high surface area folded or sandwiched AC/DC electrokinetic microelectrode array chip flip-chip bonded to a detection-sensor chip and other components that can be added or dropped into other containers with other sample solutions.

In some example embodiments, a system, device and/or method includes a method involving the use of electrochemical deposition to achieve a thick film followed by a pulsed laser surface melt to achieve greater flatness, robustness and resistance to degradation by electrolysis products.

The disclosed systems, devices and methods can be applied in a variety of applications. Some examples include blood draw, storage and transport to the clinical laboratory. For example, the disclosed devices are capable of carrying out the more immediate analysis of certain specific biomarkers. By way of just one example, the immediate measurement and reporting of the cf-DNA level in the blood is valuable as this often indicates that serious pathology or other problems exists. For example, the example systems and devices can be operated in un-diluted blood and other high conductance sample solutions provides major advantages over conventional systems. Other example attributes include that, in addition to blood draw tubes, blood collection bags and other blood storage containers, the disclosed devices can be incorporated or simply added (dropped into) urine collection tubes, and other collection tubes and containers used for many other clinical, biological and/or research applications.

In some embodiments in accordance with the present technology (example 1), an electronic device for biomarker analysis in a biofluid includes an electrokinetic microelectrode array chip operable to separate and isolate a biomarker in a biofluid using one or both of AC dielectrophoretic (DEP) and DC electrophoretic based forces, the electrokinetic microelectrode array chip including: a support structure, an array of microelectrodes coupled to a first side of the support structure, a permeation layer at least partially formed on the array of microelectrodes over the support structure, and one or more detectors, sensors, and/or emitters coupled to a second side of the support structure, wherein the electrokinetic microelectrode array chip includes a folded or a sandwiched configuration of the array of microelectrodes on the first side of the support structure and the one or more detectors, sensors, emitters, or combination thereof on the second side of the support structure that forms a microfluidic channel, and wherein the electrokinetic microelectrode array chip device is able to be incorporated within a container to hold the biofluid.

Example 2 includes the device of any of examples 1-20, wherein the one or more detectors, sensors, and/or emitters includes at least one of a uv/vis light emitter, a fluorescent detector, or a chemical sensor.

Example 3 includes the device of any of examples 1-20, wherein the electronic device further includes a housing that surrounds the electrokinetic microelectrode array chip, a power unit, and an electronic control unit.

Example 4 includes the device of any of examples 1-20, wherein the electronic control unit includes a frequency generator and an RF transmitter.

Example 5 includes the device of any of examples 1-20, wherein the electronic control unit includes a processing unit comprising a processor and a memory.

Example 6 includes the device of any of examples 1-20, wherein the electronic device further includes a fluidic sensor operable to detect a fluidic parameter of the biofluid.

Example 7 includes the device of any of examples 1-20, wherein the electronic device further includes a microfluidic pump operable to draw the biofluid into and/or out of the electrokinetic microelectrode array chip.

Example 8 includes the device of any of examples 1-20, wherein the electrokinetic microelectrode array chip provides a high surface area based on the folded or sandwiched configuration.

Example 9 includes the device of any of examples 1-20, wherein the electrokinetic microelectrode array chip is flip-chip bonded to a detection-sensor chip.

Example 10 includes the device of any of examples 1-20, wherein the electrokinetic microelectrode array chip is incorporated and packaged in a fluid collection tube.

Example 11 includes the device of any of examples 1-20, wherein the fluid collection tube includes a blood draw collection tube, and the device is operable to isolate, concentrate and protect the biomarker for analysis, including a later analysis in a clinical laboratory.

Example 12 includes the device of any of examples 1-20, wherein the fluid collection tube includes a blood draw collection tube, and the detector-sensor chip component is operable to carry out an immediate detection of the biomarker.

Example 13 includes the device of any of examples 1-20, wherein the permeation layer includes one or more of porous glass, sintered glass, or silica.

Example 14 includes the device of any of examples 1-20, wherein the permeation layer includes porous and sintered quartz and has conductive properties.

Example 15 includes the device of any of examples 1-20, wherein the biofluid is undiluted blood.

Example 16 includes the device of any of examples 1-20, wherein the biomarker is one or more of cell free (cf) DNA, RNA, nucleosomes, exosomes, extracellular vesicle (EVs), drug delivery nanoparticles, cell organelles, proteins, enzymes, protein complexes, virus, bacteria, and cancer cells.

Example 17 includes the device of any of examples 1-20, comprising from five to ten electrokinetic microelectrode array chips in the folded or sandwiched configuration.

Example 18 includes the device of any of examples 1-20, wherein the electrokinetic microelectrode array chips are 1 cm by 1.5 cm.

Example 19 includes the device of any of examples 1-20, wherein the microfluidic channel between the five to ten electrokinetic microelectrode array chips is between about 0.1 mm to about 1 mm.

Example 20 includes the device of any of examples 1-19, wherein the microfluidic channel between the five to ten electrokinetic microelectrode array chips is between about 0.2 mm.

In some embodiments in accordance with the present technology (example 21), a method of analyzing one or more biomarkers in a biofluid includes obtaining a biofluid from a subject, wherein the biofluid is placed in a collection tube including an electrokinetic microelectrode array including a support structure, an array of microelectrodes coupled to a first side of the support structure, a permeation layer at least partially formed on the array of microelectrodes over the support structure, and one or more detectors, sensors, and/or emitters coupled to a second side of the support structure, wherein the electrokinetic microelectrode array includes a folded or a sandwiched configuration of the array of microelectrodes on the first side of the support structure and the one or more detectors, sensors, emitters, or combination thereof on the second side of the support structure that forms a microfluidic channel; contacting the biofluid with the electrokinetic microelectrode array to separate and isolate the one or more biomarkers in the electrokinetic microelectrode array, wherein the electrokinetic microelectrode array separates and isolates the one or more biomarker(s) from the biofluid using one or both of AC dielectrophoretic (DEP) and DC electrophoretic based forces; and analyzing the one or more biomarkers in the biofluid.

Example 22 includes the method of any of examples 21-31, comprising introducing a stabilizing buffer onto the electrokinetic electrode array containing the one or more biomarkers to stabilize the one or more biomarkers for storage, transport, or both.

Example 23 includes the method of any of examples 21-31, wherein electrokinetic microelectrode array is operable to carry out an immediate detection of the one or more biomarkers.

Example 24 includes the method of any of examples 21-31, wherein the immediate detection of the one or more biomarkers is reported via an RF signal to a cellular device.

Example 25 includes the method of any of examples 21-31, comprising transporting the one or more biomarkers in the electrokinetic electrode array to a clinical setting, removing the one or more biomarkers from the electrokinetic electrode array, and analyzing the one or more biomarkers.

Example 26 includes the method of any of examples 21-31, wherein the analysis includes one or more of immunofluorescent detection, PCR, RT PCR analysis of RNA, DNA sequencing and epigenetic analyses, or DNA genotyping.

Example 27 includes the method of any of examples 21-31, wherein the one or more biomarkers is one or more of cell free (cf) DNA, RNA, nucleosomes, exosomes, extracellular vesicle (EVs), drug delivery nanoparticles, cell organelles, proteins, enzymes, protein complexes, virus, bacteria, or cancer cells.

Example 28 includes the method of any of examples 21-31, wherein the biofluid is blood, buffy coat blood, plasma, serum, urine, saliva, and cerebrospinal fluid (CSF).

Example 29 includes the method of any of examples 21-31, wherein about 1 mL to about 5 mL of the biofluid is obtained from the subject.

Example 30 includes the method of any of examples 21-31, wherein the biofluid is unprocessed blood.

Example 31 includes the method of any of examples 21-30, wherein about 1 mL to about 5 mL of unprocessed blood is obtained from the subject.

In some embodiments in accordance with the present technology (example P1), an electronic device for biomarker analysis in a biofluid includes an electrokinetic microelectrode array chip operable to separate and isolate a biomarker in a biofluid using one or both of AC dielectrophoretic (DEP) and DC electrophoretic based forces for concentration and/or storage of the biomarker, wherein the electrokinetic microelectrode array chip device is incorporated within a container to hold the biofluid.

Example P2 includes the device of any of examples P1-P10, wherein the electrokinetic microelectrode array chip includes: a support structure, an array of microelectrodes coupled to a first side of the support structure, a permeation layer at least partially formed on the array of microelectrodes over the support structure, and one or more detectors, sensors, and/or emitters coupled to a second side of the support structure, wherein the electrokinetic microelectrode array chip includes a folded or a sandwiched configuration of the array of microelectrodes on the first side of the support structure and the one or more detectors, sensors, and/or emitters on the second side of the support structure that forms a microfluidic channel.

Example P3 includes the device of any of examples P1-P10, wherein the one or more detectors, sensors, and/or emitters includes at least one of a uv/vis light emitter, a fluorescent detector, or a chemical sensor.

Example P4 includes the device of any of examples P1-P10, wherein electrokinetic microelectrode array chip includes one or more of: a device substrate, a power unit, an electronic control unit including a frequency generator and an RF transmitter, one or more fluid reservoirs to store a buffer fluid and/or a reagent fluid, a fluidic sensor, and/or a microfluidic pump.

Example P5 includes the device of any of examples P1-P10, wherein the electrokinetic microelectrode array chip provides a high surface area based on the folded or sandwiched configuration.

Example P6 includes the device of any of examples P1-P10, wherein the electrokinetic microelectrode array chip is flip-chip bonded to a detection-sensor chip.

Example P7 includes the device of any of examples P1-P10, wherein the electrokinetic microelectrode array chip is incorporated and packaged in a fluid collection tube.

Example P8 includes the device of any of examples P1-P10, wherein the fluid collection tube includes a blood draw collection tube, and the device is operable to isolate, concentrate and protect the biomarker for analysis, including a later analysis in a clinical laboratory.

Example P9 includes the device of any of examples P1-P10, wherein the fluid collection tube includes a blood draw collection tube, and the detector-sensor chip component is operable to carry out an immediate detection of the biomarker.

Example P10 includes the device of any of examples P1-P9, wherein the biofluid is undiluted blood.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

It is intended that the specification, together with the drawings, be considered exemplary only, where exemplary means an example. As used herein, the singular forms "a", "an" and "the" are intended to include the plural forms as well, unless the context clearly indicates otherwise. Additionally, the use of "or" is intended to include "and/or", unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A method of analyzing one or more biomarkers in a biofluid, comprising:
    obtaining a biofluid from a subject, wherein the biofluid is placed in a collection tube comprising therein an electrokinetic microelectrode array including:
        a support structure,
        an array of microelectrodes coupled to a first side of the support structure,
        a permeation layer at least partially formed on the array of microelectrodes over the support structure, and
        one or more detectors, sensors, and/or emitters coupled to a second side of the support structure,
        wherein the electrokinetic microelectrode array includes a folded or a sandwiched configuration of the array of microelectrodes on the first side of the support structure and the one or more detectors, sensors, emitters, or combination thereof on the second side of the support structure that forms a microfluidic channel;
    contacting the biofluid with the electrokinetic microelectrode array to separate and isolate the one or more biomarkers in the electrokinetic microelectrode array, wherein the electrokinetic microelectrode array separates and isolates the one or more biomarker(s) from the biofluid using one or both of AC dielectrophoretic (DEP) and DC electrophoretic based forces; and
    analyzing the one or more biomarkers in the biofluid.

2. The method of claim 1, comprising introducing a stabilizing buffer onto the electrokinetic electrode array containing the one or more biomarkers to stabilize the one or more biomarkers for storage, transport, or both.

3. The method of claim 1, comprising:
    transporting the one or more biomarkers in the electrokinetic electrode array to a clinical setting,
    removing the one or more biomarkers from the electrokinetic electrode array, and
    analyzing the one or more biomarkers.

4. The method of claim 1, wherein the analysis includes one or more of immunofluorescent detection, PCR, RT PCR analysis of RNA, DNA sequencing and epigenetic analyses, or DNA genotyping.

5. The method of claim 1, wherein the one or more biomarkers is one or more of cell free (cf) DNA, RNA, nucleosomes, exosomes, extracellular vesicle (EVs), drug delivery nanoparticles, cell organelles, proteins, enzymes, protein complexes, virus, bacteria, or cancer cells, and wherein the biofluid is blood, buffy coat blood, plasma, serum, urine, saliva, or cerebrospinal fluid (CSF).

6. The method of claim 1, wherein about 1 mL to about 5 mL of the biofluid is obtained from the subject.

7. The method of claim 1, wherein the biofluid is unprocessed blood.

* * * * *